(12) United States Patent
Kahnert et al.

(10) Patent No.: US 10,781,263 B2
(45) Date of Patent: *Sep. 22, 2020

(54) ANTI-MESOTHELIN IMMUNOCONJUGATES AND USES THEREFOR

(71) Applicant: Bayer Intellectual Property GmbH, Monheim (DE)

(72) Inventors: Antje Kahnert, Wuppertal (DE); Kerstin Unterschemmann, Wuppertal (DE); Iring Heisler, Düsseldorf (DE); Charlotte Christine Kopitz, Berlin (DE); Joachim Schuhmacher, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 110 days.

This patent is subject to a terminal disclaimer.

(21) Appl. No.: 15/923,766

(22) Filed: Mar. 16, 2018

(65) Prior Publication Data

US 2018/0201690 A1 Jul. 19, 2018

Related U.S. Application Data

(63) Continuation of application No. 14/803,410, filed on Jul. 20, 2015, now abandoned, which is a continuation of application No. 13/318,138, filed as application No. PCT/EP2010/002342 on Apr. 16, 2010, now Pat. No. 9,084,829.

(30) Foreign Application Priority Data

Apr. 29, 2009 (EP) ..................................... 09005909

(51) Int. Cl.
| | |
|---|---|
| *A61K 39/00* | (2006.01) |
| *C07K 16/30* | (2006.01) |
| *A61K 47/68* | (2017.01) |

(52) U.S. Cl.
CPC .......... *C07K 16/30* (2013.01); *A61K 47/6803* (2017.08); *A61K 47/6851* (2017.08); *C07K 2317/14* (2013.01); *C07K 2317/56* (2013.01); *C07K 2317/565* (2013.01)

(58) Field of Classification Search
CPC .................................................... C07K 16/30
See application file for complete search history.

(56) References Cited

U.S. PATENT DOCUMENTS

| | | | |
|---|---|---|---|
| 1,437,180 A | 11/1922 | Hill | |
| 4,256,746 A | 3/1981 | Miyashita et al. | |
| 4,294,757 A | 10/1981 | Asai | |
| 4,307,016 A | 12/1981 | Asai et al. | |
| 4,313,946 A | 2/1982 | Powell et al. | |
| 4,315,929 A | 2/1982 | Freedmam et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,424,219 A | 1/1984 | Hashimoto et al. | |
| 4,450,254 A | 5/1984 | Isley et al. | |
| 4,474,893 A | 10/1984 | Reading | |
| 4,657,760 A | 4/1987 | Kung et al. | |
| 4,714,681 A | 12/1987 | Reading | |
| 4,816,567 A | 3/1989 | Cabilly et al. | |
| 4,925,648 A | 5/1990 | Hansen et al. | |
| 5,206,344 A | 4/1993 | Katre et al. | |
| 5,208,020 A | 5/1993 | Chari et al. | |
| 5,225,212 A | 7/1993 | Martin et al. | |
| 5,403,574 A | 4/1995 | Piwnica-Worms | |
| 5,416,064 A | 5/1995 | Chari et al. | |
| 5,514,548 A | 4/1996 | Krebber et al. | |
| 5,573,920 A | 11/1996 | Randle | |
| 5,591,828 A | 1/1997 | Bosslet et al. | |
| 5,601,819 A | 2/1997 | Wong et al. | |
| 5,723,318 A | 3/1998 | Yamaguchi et al. | |

(Continued)

FOREIGN PATENT DOCUMENTS

| | | |
|---|---|---|
| CN | 1993146 | 7/2007 |
| EP | 404097 | 6/1990 |

(Continued)

OTHER PUBLICATIONS

Strome et al., The Oncologist, 2007; 12:1084-95 (Year: 2007).*
Brand et al., Anticancer Res. 2006; 26:463-70 (Year: 2006).*
Argani, P. et al. (Dec. 2001) "Mesothelin Is Overexpressed in the Vast Majority of Ductal Adenocarcinomas of the Pancreas: Identification of a New Pancreatic Cancer Marker by Serial Analysis of Gene Expression (SAGE)," *Clin. Cancer Res.* 7(12):3862-3868.
Bentley, G. et al. (1994) "A Structural View on Immune Recognition by Antibodies," *Research in Immunology*, 145:31-36.
Bera, T., et al. (Apr. 2002) "Mesothelin in not Required for Normal Mouse Development or Reproduction," *Mol. Cell. Biol.*, 20(8):2902-2906.
Bergan, L. et al. (2007) "Development and in vitro validation of anti-mesothelin biobodies that prevent CA125/Mesothelin-dependent cell attachment," *ScienceDirect, Cancer Letters*, 255:263-274.

(Continued)

*Primary Examiner* — Sheela J. Huff
(74) *Attorney, Agent, or Firm* — Morrison & Foerster LLP

(57) ABSTRACT

The present invention provides immunoconjugates composed of antibodies, e.g., monoclonal antibodies, or antibody fragments that bind to mesothelin, that are conjugated to cytotoxic agents, e.g., maytansine, or derivatives thereof, and/or co-administered or formulated with one or more additional anti-cancer agents. The immunoconjugates of the invention can be used in the methods of the invention to treat and/or diagnose and/or monitor cancers, e.g. solid tumors, recombinant antigen-binding regions and antibodies and functional fragments containing such antigen-binding regions that are specific for the membrane-anchored, 40 kDa mesothelin polypeptide, which is overexpressed in several tumors, such as pancreatic and ovarian tumors, mesothelioma and lung cancer cells.

2 Claims, 6 Drawing Sheets

Specification includes a Sequence Listing.

(56) References Cited

U.S. PATENT DOCUMENTS

| | | |
|---|---|---|
| 5,773,280 A | 6/1998 | Mechetner et al. |
| 5,939,598 A | 8/1999 | Kucherlapati et al. |
| 6,225,325 B1 | 5/2001 | Jacob |
| 6,294,353 B1 | 9/2001 | Pack et al. |
| 6,300,064 B1 | 10/2001 | Knappik et al. |
| 6,333,410 B1 | 12/2001 | Chari et al. |
| 6,441,163 B1 | 8/2002 | Chari et al. |
| 6,653,068 B2 | 11/2003 | Frisch et al. |
| 6,667,150 B1 | 12/2003 | Rudert et al. |
| 6,692,935 B1 | 2/2004 | Pack et al. |
| 6,696,248 B1 | 2/2004 | Knappik et al. |
| 6,706,484 B1 | 3/2004 | Knappik et al. |
| 6,716,821 B2 | 4/2004 | Zhao et al. |
| 6,753,136 B2 | 6/2004 | Löhning |
| 6,809,184 B1 | 10/2004 | Pastan et al. |
| 6,828,422 B1 | 12/2004 | Achim et al. |
| 7,049,135 B2 | 5/2006 | Rudert et al. |
| RE39,151 E | 6/2006 | Chari et al. |
| 7,276,497 B2 | 10/2007 | Chari et al. |
| 7,375,183 B1 | 5/2008 | Pastan et al. |
| 7,553,494 B2 | 6/2009 | Gaiger |
| 7,592,426 B2 | 9/2009 | Ebel et al. |
| 8,128,926 B2 | 3/2012 | Mi et al. |
| 8,206,710 B2 | 6/2012 | Ebel et al. |
| 8,241,628 B2 | 8/2012 | Diefenbach-Streiber et al. |
| 9,084,829 B2 | 7/2015 | Kahnert et al. |
| 2004/0241174 A1 | 12/2004 | Amphlett et al. |
| 2005/0031614 A1 | 2/2005 | Roskos et al. |
| 2005/0276812 A1 | 12/2005 | Ebens, Jr. et al. |
| 2006/0002942 A1 | 1/2006 | Kunz |
| 2006/0099141 A1 | 5/2006 | O'Brien et al. |
| 2006/0182750 A1 | 8/2006 | Chari et al. |
| 2006/0204506 A1 | 9/2006 | Ebel et al. |
| 2007/0015837 A1 | 1/2007 | Kun et al. |
| 2007/0031402 A1 | 2/2007 | Zhang |
| 2007/0237758 A1 | 10/2007 | Barry |
| 2009/0274713 A1 | 11/2009 | Chari et al. |
| 2009/0298088 A1 | 12/2009 | Belyaev |
| 2011/0003969 A1 | 1/2011 | Kellogg et al. |
| 2012/0107933 A1 | 5/2012 | Ho et al. |
| 2012/0148576 A1 | 6/2012 | Sharma |
| 2013/0066055 A1 | 3/2013 | Lerchen |
| 2017/0327589 A1 | 11/2017 | Kahnert |
| 2018/0201690 A1 | 7/2018 | Kahnert |
| 2018/0258181 A1 | 9/2018 | Kahnert |

FOREIGN PATENT DOCUMENTS

| | | |
|---|---|---|
| JP | 2000-505787 | 5/2000 |
| JP | 2008-532523 | 8/2008 |
| JP | 2009536936 A | 11/2009 |
| NZ | 579482 | 2/2011 |
| NZ | 585551 | 6/2012 |
| RU | 2006147264 | 5/2005 |
| WO | WO-1991/00360 | 1/1991 |
| WO | WO-1992/05793 | 4/1992 |
| WO | WO-1992/08802 | 5/1992 |
| WO | WO-1993/11161 | 6/1993 |
| WO | WO-1993/17715 | 9/1993 |
| WO | WO-1994/29451 | 12/1994 |
| WO | WO-1997/08320 | 3/1997 |
| WO | WO-1997/025068 | 7/1997 |
| WO | WO-1999/28471 | 6/1999 |
| WO | WO-2000/50900 | 8/2000 |
| WO | WO-2001/05950 | 1/2001 |
| WO | WO-2001/24763 | 4/2001 |
| WO | WO-2004/004639 | 1/2004 |
| WO | WO-2004/110498 | 12/2004 |
| WO | WO-2005/117986 | 12/2005 |
| WO | WO-2006/099141 | 9/2006 |
| WO | WO-2006/122797 | 11/2006 |
| WO | WO-2006/124641 | 11/2006 |
| WO | WO-2006/130458 | 12/2006 |
| WO | WO-2007/019232 | 2/2007 |
| WO | WO2007054551 A1 | 5/2007 |
| WO | WO2007131972 A1 | 11/2007 |
| WO | WO-2009/045957 | 4/2009 |
| WO | WO-2009/068204 | 6/2009 |
| WO | WO-2010/008726 | 1/2010 |
| WO | WO-2010/124797 | 11/2010 |
| WO | WO2012143495A2 A2 | 10/2012 |
| WO | WO2012143495A3 A3 | 10/2012 |
| WO | WO-2015/059147 | 4/2015 |

OTHER PUBLICATIONS

Beyer, H. et al. (2007) "MESOMARK: A Potential Test for Malignant Pleural Mesothelioma," *Clinical Chemistry*, 53(4):666-672.

Bradley, G. et al. (1988) "Mechanism of multidrug resistance," *Biochinica et Biophysica Acta.*, 948:87-128.

Brooks, P. et al. (Apr. 22, 1994) "Requirement of Vascular Integrin $\alpha_v\beta_3$ for Angiogenesis," *Science*, 264:569-570.

Brown, M. et al. (1996) "Tolerance to Single, but Not Multiple, Amino Acid Replacements in Antibody $V_H$ CDR2," *J Immunol.*, 156:3285-3291.

Cao, Y. (1998) "Endogenous Angiogenesis Inhibitors: Angiostatin, Endostatin, and Other Proteolytic Fragments," Progress in Molecular and Subcellular Biology, 20:161-176.

Casset, F. et al. (2003) "A peptide mimetic of an anti-CD4 monoclonal antibody by rational design," *BBRC*, 307:198-205.

Chang, K. et al. (1992) "Isolation and Characterization of a Monoclonal Antibody, K1, Reactive with Ovarian Cancers and Normal Mesothelium," *Int. j. cancer*, 50:373-381.

Chang, K. et al. (Jan. 1996) "Molecular cloning of mesothelin, a differentiation antigen present on mesothelium, mesotheliomas, and ovarian cancers," *Proc. Natl. Acad. Sci. USA*, 93:136-140.

Chen, C. et al. (Nov. 7, 1986) "Internal Duplication and Homology with Bacterial Transport Proteins in the mdr1 (P-Glycoprotein) Gene from Multidrug-Resistant Human Cells," *Cell*, 47:381-389.

Chi, E. et al. (Sep. 2003) Physical Stability of Proteins in Aqueous Solution: Mechanism and Driving Forces in Nonnative Protein Aggregation, *Pharmaceutical Research*, 20(9):1325-1336.

Clackson, T. et al. (Aug. 15, 1991) "Making antibody fragments using phage display libraries," *Nature*, 352:624-628.

Croop, J. et al. (May 1988) "Genetics of Multidrug Resistance," *J. clin. Invest.*, 81:1303-1309.

Crowley, C. et al. (Jun. 1993) "Prevention of metastasis by inhibition of the urokinase receptor," Proc. Natl. Acad. Sci. USA, 90:5021-5025.

Davies, J. et al. (1996) "Affinity improvement of single antibody VH domains: residues in all three hypervariable regions affect antigen binding," Immunol., 2:169-179.

de Pascalis, R. et al. (2002) "Grafting of "Abbreviated" Complementarity-Determining Regions Containing Specificity-Determining Residues Essential for Ligand Contact to Engineer a Less Immunogenic Humanized Monoclonal Antibody," *J Immunol.*, 169:3076-3084.

Deshmukh, P., et al. (Feb. 2001) "Immunogene therapy with interleukin-2-secreting fibroblasts for intracerebrally metastasizing breast cancer in mice," *J Neurosurg*, 94:287-292.

Erickson, H. et al. (Apr. 15, 2006) "Antibody-Maytansinoid Conjugates are Activated in Targeted Cancer Cells by Lysosomal Degradation and Linker-Dependent Interacellular Processing," *Cancer Res*, 66(8):4426-4433.

Extended European Search Report and Written Opinion dated Feb. 9, 2018 for European Application No. EP17189537.8, filed Apr. 16, 2010, 13 pages.

Extended European Search Report and Written Opinion, dated Nov. 16, 2015 for European Application No. EP16170412.7, filed Nov. 19, 2008, 11 pages.

Fan, D., et al. (Jun. 2002) "Targeted Therapy against Human Lung Cancer in Nude Mice by High-Affinity Recombinant Antimesothelin Single-Chain Fv Immunotoxin," *Molecular Cancer Therapeutics*, 1:595-600.

Filpula, D. et al. (2007) "Releasable PEGylation of Mesothelin Targeted Immunotoxin SS1P Achieves Single Dosage Complete Regression of a Human Carcinoma in Mice," *Bioconjugate Chem.*, 18:773-784.

(56) References Cited

OTHER PUBLICATIONS

Gottesman, M., et al. (Feb. 1988) "Resistance to multiple chemotherapeutic agents in human cancer cells," *TIPS*, 9:54-58.
Gottesman, M., et al. (Sep. 5, 1988) "The Multidrug Transporter, a Double-edged Sword," *J Biol Chem.*, 263(25):12163-12166.
Griswold, D. P. et al. (1981) "Clonogenicity and Growth of Experimental Tumors in Relation of Developing Resistance and Therapeutic Failure," *Cancer Treat. Rep.*, 65(S2):51-54.
Gros, P. et al. (1986) "Mammalian Multidrug Resistance Gene: Complete cDNA Sequence Indicates Strong Homology to Bacterial Transport Proteins," *Cell* 47:371-380.
Güssow, D., et al. (1991) "Humanization of Monoclonal Antibodies," *Methods in Enzymology*,203:99-121.
Haenel, C., et al. (2005) "Characterization of high-affinity antibodies by electrochemiluminescence-based equilibrium titration," 339:182-184.
Hale, W., et al. (1991) "The Harper Collins Dictionary of Biology, Imprint" 5 pages.
Hammes, H., et al. (May 1996) "Subcutaneous injection of a cyclic peptide antagonist of vitronectin receptor-type integrins inhibits retinal neovascularization," *Nature medicine*, 2(5):529-533.
Hassan R. et al. (2000) "Anti-Tumor Activity of K1-LysPE38QQR, an Immunotoxin Targeting Mesothelin, a Cell-Surface Antigen Overexpressed in Ovarian Cancer and Malignant Mesothelioma, " *J Immunotherapy*, 23(4): 473-479.
Hassan, R. et al. (2008) "Mesothelin targeted cancer immunotherapy," *Europ J Cancer* 44:46-53.
Hassan, R., et al. (Jun. 15, 2004) "Mesothelin: A New Target for Immunotherapy," Clin Cancer Res, 10:3937-3942.
Hassan, R., et al. (Nov. 2002) "Antitumor Activity of SS(dsFv)PE38 and SS1(dsFv)PE38, Recombinant Antimesothelin Immunotoxins against Human Gynecologic Cancers Grown in Organotypic Culture in vitro[1]," *Clin Cancer Res*, 8:3520-3526.
Hellstrom, I., et al. (2006) "Mesothelin Variant 1 is Released from Tumor Cells as a Diagnostic Marker," *Cancer Epidemiol Biomarkers Prev*, 15 (5): 1014-1020.
Herzog, H., et al. (Dec. 1993) "Measurement of Pharmacokinetics of Yttrium-86 Radiopharmaceuticals with PET and Radiation Dose Calculation of Analogous Yttrium-90 Radiotherapeutics," *J. Nucl. Med.*, 34(12):2222-2226.
Ho, M., et al., (Mar. 1, 2007) "Mesothelin Expression in Human Lung Cancer," *Clin. Cancer Res.*, 13 (5): 1571-1575.
Holliger, P., et al. (Jul. 1993) "Diabodies: Small bivalent and bispecific antibody fragments," *Proc. Natl. Acad. Sci. USA*, 90:6444-6448.
Holliger, P., et al. (Sep. 2005) "Engineered antibody fragments and the rise of single domains," *Nat. Biotechnol*, 23(9):1126-1136.
Holm, P., et al., (2007) "Functional mapping and single chain construction of the anti-cytokeratin 8 monoclonal antibody TS1," *Mol. Immunol.*, 44:1075-1084.
Holt, L., et al. (Nov. 2003) "Domain antibodies: proteins for therapy," *TRENDS in Biotechnology*, 21(11):484-490.
International Preliminary Report dated Jun. 10, 2010 for International Application No. PCT/EP2008/009756, filed Nov. 19, 2008, 9 pages.
International Preliminary Report dated May 6, 2016 for International Application No. PCT/EP2014/072558, filed Oct. 21, 2014, 8 pages.
International Search Report and Written Opinion dated Apr. 8, 2009 for International Application No. PCT/EP2008/009756, filed Nov. 19, 2008, 18 pages.
International Search Report and Written Opinion dated Aug. 3, 2010 for International Application No. PCT/EP2010/002342, filed Apr. 16, 2010, 15 pages.
International Search Report and Written Opinion dated Jan. 20, 2015 for International Application No. PCT/EP2014/072558, filed Oct. 21, 2014, 9 pages.
Jones, P., et al. (May 29, 1986) "Replacing the complementarity-determining regions in a human antibody with those from a mouse," *NATURE*, 321:522-525.
Juranka, P., et al. (Dec. 1989) "P-glycoprotein: multidrug-resistance and a superfamily of membrane-associated transport proteins," *The FASEB Journal*, 3:2583-2592.
Khorana, H., et al. (1972) "Studies on Polynucleotides CIII. Total Synthesis of the Structural Gene for an Alanine Transfer Ribonucleic Acid from Yeast," *J. Mol. Biol.*, 72:209-217.
Knappik, A., et al. (2000) "Fully Synthetic Human Combinatorial Antibody Libraries (HuCAL) Based on Modular Consensus Frameworks and CDRs Randomized with Trinucleotides," *J. Mol. Biol.*, 296:57-86.
Köhler, G., et al. (Aug. 7, 1975) "Continuous cultures of fused cells secreting antibody of predefined specificity," Nature, 256:495-497.
Kostelny, S., et al. (Mar. 1, 1992) "Formation of a Bispecific Antibody by the use of Leucine Zippers," *J. Immunol.*, 148(5): 1547-1553.
Kovtun, Y., et al. (Mar. 15, 2006) "Antibody-Drug Conjugates Designed to Eradicate Tumors with Homogeneous and Heterogeneous Expression of the Target Antigen," *Cancer Res.*, 66(6):3214-3221.
Kreds, B., et al. (2001) "High-throughput generation and engineering of recombinant human antibodies," *J. Immunol. Methods.*, 254(1-2):67-84.
Kuus-Reichel, K., et al. (Jul. 1994) "Will Immunogenicity Limit the Use, Efficacy, and Future Development of Therapeutic Monoclonal Antibodies?" *Clin. Diagn. Lab. Immunol.*, 1(4):365-372.
Lavie, Y., et al. (Aug. 9, 1996) "Accumulation of Glucosylceramides in Multidrug-resistant Cancer Cells," *J. Bio. Chem.*, 271(32):19530-19536.
Liao, S., et al. (1997) "Identification of the MN/CA9 Protein As a Reliable Diagnostic Biomarker of Clear Cell Carcinoma of the Kidney," *Cancer Res.*, 57:2827-2831.
Liao, S., et al. (Sep. 1994) "Identification of the MN Antigen as a Diagnostic Biomarker of Cervical Intraepithelial Squamous and Glandular Neoplasia and Cervical Carcinomas," *Am. J. Pathol.*, 145(3):598-609.
MacCallum, R., et al. (1996) "Antibody-antigen Interactions: Contact Analysis and Binding Site Topography," *J. Mol. Biol.*, 262:732-745.
Maione, T., et al. (Apr. 15, 1991) "Inhibition of Tumor Growth in Mice by an Analogue of Platelet Factor 4 That Lacks Affinity for Heparin and Retains Potent Angiostatic Activity," *Cancer Res.*, 51:2077-2083.
Mariuzza, R., et al. (1987) "The Structural Basis of Antigen-Antibody Recognition," *Ann. Rev. Biophys. Biophys. Chem.*, 16:139-159.
Marks, J., et al. (1991) "By-passing Immunization Human Antibodies from V-gene Libraries Displayed on Phage," *J. Mol. Biol.*, 222:581-597.
Min, H., et al. (May 15, 1996) "Urokinase Receptor Antagonists Inhibit Angiogenesis and Primary Tumor Growth in Syngeneic Mice," *Cancer Res.*, 56:2428-2433.
Mirski, S., et al. (May 15, 1987) "Multidrug Resistance in a Human Small Cell Lung Cancer Cell Line Selected in Adriamycin," *Cancer Res.*, 47:2594-2598.
Morrison, S., et al. (Nov. 1984) "Chimeric human antibody molecules: Mouse antigen-binding domains with human constant region domains," *Proc. Natl. Acad. Sci. USA*, 81:6851-6855.
Moscow, J., et al. (Mar. 2, 1988) "Multidrug Resistance," *J. Natl. Cancer Inst.*, 80(1):14-20.
Muminova, Z., et al. (May 12, 2004) "Characterization of human mesothelin transcripts in ovarian and pancreatic cancer," *BMC Cancer*, 4:1-10.
Onda, M., et al. (Aug. 15, 2005) "New Monoclonal Antibodies to Mesothelin Useful for Immunohistochemistry, Fluorescence-Activated Cell Sorting, Western Blotting, and ELISA," *Clin. Cancer Res.*, 11(16):5840-5846.
Osteen, T., et al. (1990) "Cancer Manual," Table of Contents, *American Cancer Society*, 8 pages.
Paul, W., (1993) "Fundamental Immunology," *Raven Press*, 3rd Edition, 292-295.
Plückthun, A., (1994) "Antibodies from *Escherichia coli*," *Handbook of Experimental Pharmacology*, 113:269-315.

(56) References Cited

OTHER PUBLICATIONS

Polakis, P. (2005) "Arming antibodies for cancer therapy," *Current Opinion in Pharmacology*, 5:382-387.
Presta, L. (1992) "Antibody engineering," *Current Opinion in Structural Biology*, 2:593-596.
Rauchenberger, R., et al. (Oct. 3, 2003) "Human Combinatorial Fab Library Yielding Specific and Functional Antibodies against the Human Fibroblast Growth Factor Receptor 3," *J. Bio. Chem.*, 278(40):38194-38205.
Riechmann, L. et al. (Mar. 24, 1988) "Reshaping human antibodies for therapy," *Nature*, 332:323-327.
Riordan, J., et al. (1985) "Genetic and Biochemical Characterization of Multidrug Resistance," *Pharmac. Ther.*, 28:51-75.
Riva, P., et al. (Oct. 1999) "Loco-Regional Radioimmunotherapy of High-Grade Malignant Gliomas Using Specific Monoclonal Antibodies Labeled with $^{90}$Y: A Phase I Study," *Clin. Cancer Res.*, 5:3275s-3280s.
Robbins, P., et al. (1996) "Human tumor antigens recognized by T cells," *Curr. Opin. Immunol.*, 8:628-636.
Rudikoff, S., et al. (Mar. 1982) "Single amino acid substitution altering antigen-binding specificity," *Pro. Natl. Acad. Sci. USA*, 79:1979-1983.
Rump, A., et al. (Mar. 5, 2004) "Binding of Ovarian Cancer Antigen CA125/MUC16 to Mesothelin Mediates Cell Adhesion," *J. Bio. Chem.*, 279(10):9190-9198.
Saarnio, J., et al. (Jul. 1998) "Immunohistochemical Study of Colorectal Tumors for Expression of a Novel Transmembrane Carbonic Anhydrase, MN/CA IX, with Potential Value as a Marker of Cell Proliferation," *Am. J. Pathol.*, 153(1):279-285.
Sage, E., et al. (Jan. 1995) "Inhibition of endothelial cell proliferation by SPARC is mediated through a Ca(2+)-binding EF-hand sequence," Abstract, *J. Cell Biochem.*, 57(1):127-140.
Scholler, N., et al. (2007) "Development of a CA125-mesothelin cell adhesion assay as a screening tool for biologics discovery," *Cancer Letters*, 247:130-136.
Sodee, B., et al. (1996) "Preliminary Imaging Results Using In-111 Labeled CYT-356 (Prostascint™) in the Detection of Recurrent Prostate Cancer," *Clin. Nuc. Med.*, 21(10):759-766.
Teng, Y., et al. (Feb. 2008) "CD20 epitope masking by rituximab: comment on the article by Gunnarsson et al," *Arthritis Rheum.*, 58(2)"634-636.
Tolsma, S., et al. (Jul. 1993) "Peptides Derived from Two Separate Domains of the Matrix Protein Thrombospondin-1 Have Anti-Angiogenic Activity," *J. Cell Biol.*, 122(2):497-511.
Turner, J., et al. (Jun. 1997) "MN Antigen Expression in Normal, Preneoplastic, and Neoplastic Esophagus: A Clinicopathological Study of a New Cancer-Associated Biomarker," *Human Path.*, 28(6):740-744.
Tutt, A., et al. (Jul. 1, 1991) "Trispecific F(ab')$_3$ Derivatives that use Cooperative Signaling Via the TCR/CD3 Complex and CD2 to Activate and Redirect Resting Cytotoxic T Cells," *J. Immunol.*, 147(1) ;60-69.
Vajdos, F., et al. (2002) "Comprehensive Functional Maps of the Antigen-binding Site of an Anti-ErbB2 Antibody Obtained with Shotgun Scanning Mutagenesis,"*J. Mol. Biol.*, 320:415-428.
Vermylen, P., et al. (1999) "Carbonic anhydrase IX antigen differentiates between preneoplastic malignant lesions in non-small cell lung carcinoma," *Eur. Respir. J.*, 14:806-811.
Virnekas, B., et al. (1994) "Trinucleotide phosphoramidites: ideal reagents for the synthesis of mixed oligonucleotides for random mutagenesis," *Nucl. Acids Res.*, 22(25):5600-5607.
Wagner, H., et al. (Feb. 2002) "Administration Guidelines for Radioimmunotherapy of Non-Hodgkin's Lymphoma with $^{90}$Y-Labeled Anti-CD20 Monoclonal Antibody," *J. Nucl.Med.*, 43(2):267-272.
Wang, W. (2002) "Lyophilization and development of solid protein pharmaceuticals," *Int. J. Pharm.*, 203:1-60.
Wittes, R., et al. (Jan. 1986) "Unresolved Issues in Combination Chemotherapy," *Cancer Treatment Reports*, 70(1):105-125.
Wong, J., et al. (Oct. 2000) "A Phase I Radioimmunotherapy Trial Evaluating $^{90}$Yttrium-labeled Anti-Carcinoembryonic Antigen (CEA) Chimeric T84.66 in Patients with Metastatic CEA-producing Malignancies[1]," *Clin. Cancer Res.*, 6:3855-3863.
Zapata, G., et al. (1995) "Engineering Linear F(ab')$_2$ fragments for efficient production in *Escherichia coli* and enhanced antiproliferative activity," *Protein Engineering*, 8(10):1057-1062.
Abbas et al. (1994). Cellular and Molecular Immunology, 2nd Edition, List of Contents, 5 pages.
Almagro, J.C. et al. (Jan. 1, 2008). "Humanization of Antibodies," Frontiers in Bioscience 13:1619-1633.
Carter, P.J. (May 2006). "Potent Antibody Therapeutics by Design," Nat Rev Immunol 6:343-357.
Greenspan, N.S. et al. (Oct. 1999). "Structural Analysis: Defining Epitopes: It's Not As Easy As It Seems," Nature Biotechnology 17:936-937.
Harlow, E. et al. (1988). Antibodies A Laboratory Manual, Table of Contents only.
Lackie, J.M. et al. (1999). The Dictionary of Cell and Molecular Biology, Third Edition, Table of Content.
Mahler, H.-C.et al. (2005, e-pub. Jan. 19, 2005). "Induction and Analysis of Aggregates In a Liquid IgG1—Antibody Formulation," European Journal of Pharmaceutics and Biopharmaceutics 59:407-417.
Remington: The Science and Practice of Pharmacy (2000). 20th ed., Daniel Limmer ed., Baltimore, Maryland—List of Contents.
Singleton, P. et al. (1994). Dictionary of Microbiology and Molecular Biology, 2nd ed. New York, New York.
The Cambridge Dictionary of Science and Technology, (1988). P.M.B. Walker ed. New York, New York—List of Contents.
U.S. Preliminary Amendment filed on Jun. 1, 2018, for U.S. Appl. No. 15/911,748, filed Mar. 5, 2018, 19 pages.
U.S. Response to Office Action filed on Jan. 9, 2019, for U.S. Appl. No. 15/656,645, filed Jul. 21, 2017, 20 pages.
Warne, N.W. et al. (2011, e-pub. Mar. 13, 2011). "Development of High Concentraction Proteing Biopharmaceuticals: The Use of Platform Approaches in Formulation Development," European Journal of Pharmaceutics and Biopharmaceutics 78:208-212.
Brand, F.X. et al. (2006). "Prospect for Anti-HER2 Receptor Therapy in Breast Cancer" Anticancer Res. 26:463-470.
Strome et al. (2007). "A Mechanistic Perspective of Monoclonal Antibodies in Cancer Therapy Beyond Target-Related Effects" Oncologist 12:1084-1095.
Wang, W. et al. (Jan. 2007). "Antibody Structure, Instability, and Formulation," Journal of Pharmaceutical Science 96(1):1-26.

\* cited by examiner

SEQUENCE LISTING

<160> NUMBER OF SEQ ID NOS: 36

<210> SEQ ID NO 1
<211> LENGTH: 10
<212> TYPE: PRT
<213> ORGANISM: Homo sapiens

<400> SEQUENCE: 1

Gly Tyr Ser Phe Thr Asn Tyr Trp Ile Gly
1               5                   10

<210> SEQ ID NO 2
<211> LENGTH: 10
<212> TYPE: PRT
<213> ORGANISM: Homo sapiens

<400> SEQUENCE: 2

Gly Tyr Thr Phe Thr Gly Asn Tyr Ile Asn
1               5                   10

<210> SEQ ID NO 3
<211> LENGTH: 10
<212> TYPE: PRT
<213> ORGANISM: Homo sapiens

<400> SEQUENCE: 3

Gly Tyr Ser Phe Thr Ser Tyr Trp Ile Gly
1               5                   10

<210> SEQ ID NO 4
<211> LENGTH: 20
<212> TYPE: PRT
<213> ORGANISM: Homo sapiens

<400> SEQUENCE: 4

Trp Met Gly Val Ile Met Pro Ser Asp Ser Tyr Thr Arg Tyr Ser Pro
1               5                   10                  15

Ser Phe Gln Gly
            20

<210> SEQ ID NO 5
<211> LENGTH: 20
<212> TYPE: PRT
<213> ORGANISM: Homo sapiens

<400> SEQUENCE: 5

Trp Met Gly Ile Ile Asn Pro His Gly Gly Asp Thr Lys Tyr Ala Gln
1               5                   10                  15

Lys Phe Gln Gly
            20

<210> SEQ ID NO 6
<211> LENGTH: 20
<212> TYPE: PRT
<213> ORGANISM: Homo sapiens

<400> SEQUENCE: 6

Trp Met Gly Ile Ile Asp Pro Gly Asp Ser Arg Thr Arg Tyr Ser Pro
1               5                   10                  15

Ser Phe Gln Gly
            20

<210> SEQ ID NO 7

```
<211> LENGTH: 12
<212> TYPE: PRT
<213> ORGANISM: Homo sapiens

<400> SEQUENCE: 7

Tyr Gly His Gly Met Tyr Gly Gly Ala Leu Asp Val
1               5                   10

<210> SEQ ID NO 8
<211> LENGTH: 10
<212> TYPE: PRT
<213> ORGANISM: Homo sapiens

<400> SEQUENCE: 8

Trp His His Gly Thr Trp Ile Phe Asp Tyr
1               5                   10

<210> SEQ ID NO 9
<211> LENGTH: 11
<212> TYPE: PRT
<213> ORGANISM: Homo sapiens

<400> SEQUENCE: 9

Gly Gln Leu Tyr Gly Gly Thr Tyr Met Asp Gly
1               5                   10

<210> SEQ ID NO 10
<211> LENGTH: 12
<212> TYPE: PRT
<213> ORGANISM: Homo sapiens

<400> SEQUENCE: 10

Arg Ala Ser Gln Ser Val Arg Ser Ser Arg Leu Ala
1               5                   10

<210> SEQ ID NO 11
<211> LENGTH: 13
<212> TYPE: PRT
<213> ORGANISM: Homo sapiens

<400> SEQUENCE: 11

Ser Gly Ser Ser Ser Asn Ile Gly Ser Asn Tyr Val Ser
1               5                   10

<210> SEQ ID NO 12
<211> LENGTH: 14
<212> TYPE: PRT
<213> ORGANISM: Homo sapiens

<400> SEQUENCE: 12

Thr Gly Thr Ser Ser Asp Ile Gly Gly Tyr Asn Ser Val Ser
1               5                   10

<210> SEQ ID NO 13
<211> LENGTH: 11
<212> TYPE: PRT
<213> ORGANISM: Homo sapiens

<400> SEQUENCE: 13

Leu Leu Ile Tyr Gly Ala Ser Lys Arg Ala Thr
1               5                   10

<210> SEQ ID NO 14
<211> LENGTH: 11
<212> TYPE: PRT
```

```
<213> ORGANISM: Homo sapiens

<400> SEQUENCE: 14

Leu Leu Ile Tyr Asn Asp Asn Gln Arg Pro Ser
1               5                   10

<210> SEQ ID NO 15
<211> LENGTH: 11
<212> TYPE: PRT
<213> ORGANISM: Homo sapiens

<400> SEQUENCE: 15

Leu Met Ile Tyr Gly Val Asn Asn Arg Pro Ser
1               5                   10

<210> SEQ ID NO 16
<211> LENGTH: 8
<212> TYPE: PRT
<213> ORGANISM: Homo sapiens

<400> SEQUENCE: 16

Gln Gln Tyr Tyr Asp Phe Pro Pro
1               5

<210> SEQ ID NO 17
<211> LENGTH: 9
<212> TYPE: PRT
<213> ORGANISM: Homo sapiens

<400> SEQUENCE: 17

Gln Gln Tyr Ser His Asp Pro Ser Gly
1               5

<210> SEQ ID NO 18
<211> LENGTH: 9
<212> TYPE: PRT
<213> ORGANISM: Homo sapiens

<400> SEQUENCE: 18

Ser Thr Tyr Asp Arg Arg Thr Phe Ser
1               5

<210> SEQ ID NO 19
<211> LENGTH: 10
<212> TYPE: PRT
<213> ORGANISM: Homo sapiens

<400> SEQUENCE: 19

Ser Ser Tyr Asp Ile Glu Ser Ala Thr Pro
1               5                   10

<210> SEQ ID NO 20
<211> LENGTH: 121
<212> TYPE: PRT
<213> ORGANISM: Homo sapiens

<400> SEQUENCE: 20

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45
```

```
Gly Val Ile Met Pro Ser Asp Ser Tyr Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr Gly His Gly Met Tyr Gly Gly Ala Leu Asp Val Trp Gly
                100                 105                 110

Gln Gly Thr Leu Val Thr Val Ser Ser
            115                 120

<210> SEQ ID NO 21
<211> LENGTH: 121
<212> TYPE: PRT
<213> ORGANISM: Homo sapiens

<400> SEQUENCE: 21

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asn Tyr
                 20                  25                  30

Trp Ile Gly Trp Val Arg Gln Met Pro Gly Lys Gly Leu Glu Trp Met
             35                  40                  45

Gly Val Ile Met Pro Ser Asp Ser Tyr Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr Gly His Gly Met Tyr Gly Gly Ala Leu Asp Val Trp Gly
                100                 105                 110

Gln Gly Thr Leu Val Thr Val Ser Ser
            115                 120

<210> SEQ ID NO 22
<211> LENGTH: 119
<212> TYPE: PRT
<213> ORGANISM: Homo sapiens

<400> SEQUENCE: 22

Gln Val Glu Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Asn
                 20                  25                  30

Tyr Ile Asn Trp Val Arg Gln Ala Pro Gly Gln Gly Leu Glu Trp Met
             35                  40                  45

Gly Ile Ile Asn Pro His Gly Gly Asp Thr Lys Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp His His Gly Thr Trp Ile Phe Asp Tyr Trp Gly Gln Gly
                100                 105                 110

Thr Leu Val Thr Val Ser Ser
            115
```

<210> SEQ ID NO 23
<211> LENGTH: 120
<212> TYPE: PRT
<213> ORGANISM: Homo sapiens

<400> SEQUENCE: 23

```
Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Ala Pro Gly Lys Gly Leu Glu Trp Met
            35                  40                  45

Gly Ile Ile Asp Pro Gly Asp Ser Arg Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gln Leu Tyr Gly Gly Thr Tyr Met Asp Gly Trp Gly Gln
            100                 105                 110

Gly Thr Leu Val Thr Val Ser Ser
            115                 120
```

<210> SEQ ID NO 24
<211> LENGTH: 110
<212> TYPE: PRT
<213> ORGANISM: Homo sapiens

<400> SEQUENCE: 24

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Arg Leu Ala Trp Tyr Gln Gln Lys Pro Gly Gln Ala Pro Arg Leu Leu
            35                  40                  45

Ile Tyr Gly Ala Ser Lys Arg Ala Thr Gly Val Pro Ala Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gly Tyr Tyr Asp Phe Pro
                85                  90                  95

Pro Thr Phe Gly Gln Gly Thr Lys Val Glu Ile Lys Arg Thr
            100                 105                 110
```

<210> SEQ ID NO 25
<211> LENGTH: 111
<212> TYPE: PRT
<213> ORGANISM: Homo sapiens

<400> SEQUENCE: 25

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Arg Leu Ala Trp Tyr Gln Gln Lys Pro Gly Gln Ala Pro Arg Leu Leu
            35                  40                  45

Ile Tyr Gly Ala Ser Lys Arg Ala Thr Gly Val Pro Ala Arg Phe Ser
```

```
                50                  55                  60
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser His Asp Pro
                 85                  90                  95

Ser Gly Thr Phe Gly Gln Gly Thr Lys Val Glu Ile Lys Arg Thr
                100                 105                 110

<210> SEQ ID NO 26
<211> LENGTH: 111
<212> TYPE: PRT
<213> ORGANISM: Homo sapiens

<400> SEQUENCE: 26

Asp Ile Val Leu Thr Gln Pro Pro Ser Val Ser Gly Ala Pro Gly Gln
 1               5                  10                  15

Arg Val Thr Ile Ser Cys Ser Gly Ser Ser Asn Ile Gly Ser Asn
                 20                  25                  30

Tyr Val Ser Trp Tyr Gln Gln Leu Pro Gly Thr Ala Pro Lys Leu Leu
                 35                  40                  45

Ile Tyr Asn Asp Asn Gln Arg Pro Ser Gly Val Pro Asp Arg Phe Ser
                 50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Ser Thr Tyr Asp Arg Thr
                 85                  90                  95

Phe Ser Val Phe Gly Gly Gly Thr Lys Leu Thr Val Leu Gly Gln
                100                 105                 110

<210> SEQ ID NO 27
<211> LENGTH: 113
<212> TYPE: PRT
<213> ORGANISM: Homo sapiens

<400> SEQUENCE: 27

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Ile Gly Gly Tyr
                 20                  25                  30

Asn Ser Val Ser Trp Tyr Gln Gln His Pro Gly Lys Ala Pro Lys Leu
                 35                  40                  45

Met Ile Tyr Gly Val Asn Asn Arg Pro Ser Gly Val Ser Asn Arg Phe
                 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Ile Glu
                 85                  90                  95

Ser Ala Thr Pro Val Phe Gly Gly Gly Thr Lys Leu Thr Val Leu Gly
                100                 105                 110

Gln

<210> SEQ ID NO 28
<211> LENGTH: 363
<212> TYPE: DNA
<213> ORGANISM: Homo sapiens

<400> SEQUENCE: 28
```

```
caggtggaat tggttcagag cggcgcggaa gtgaaaaaac cgggcgaaag cctgaaaatt      60
agctgcaaag gttccggata ttcctttact aattattgga ttggttgggt gcgccagatg     120
cctgggaagg gtctcgagtg gatgggcgtt atcatgccgt ctgatagcta tacccgttat     180
tctccgagct ttcagggcca ggtgaccatt agcgcggata aaagcattag caccgcgtat     240
cttcaatgga gcagcctgaa agcgagcgat acggccatgt attattgcgc gcgttatggt     300
catggtatgt atggtggtgc tcttgatgtt tggggccaag gcaccctggt gacggttagc     360
tca                                                                   363

<210> SEQ ID NO 29
<211> LENGTH: 363
<212> TYPE: DNA
<213> ORGANISM: Homo sapiens

<400> SEQUENCE: 29
caggtgcaat tggttcagag cggcgcggaa gtgaaaaaac cgggcgaaag cctgaaaatt      60
agctgcaaag gttccggata ttcctttact aattattgga ttggttgggt gcgccagatg     120
cctgggaagg gtctcgagtg gatgggcgtt atcatgccgt ctgatagcta tacccgttat     180
tctccgagct ttcagggcca ggtgaccatt agcgcggata aaagcattag caccgcgtat     240
cttcaatgga gcagcctgaa agcgagcgat acggccatgt attattgcgc gcgttatggt     300
catggtatgt atggtggtgc tcttgatgtt tggggccaag gcaccctggt gacggttagc     360
tca                                                                   363

<210> SEQ ID NO 30
<211> LENGTH: 357
<212> TYPE: DNA
<213> ORGANISM: Homo sapiens

<400> SEQUENCE: 30
caggtggaat tggttcagag cggcgcggaa gtgaaaaaac cgggcgcgag cgtgaaagtg      60
agctgcaaag cctccggata tacctttact ggtaattata ttaattgggt ccgccaagcc    120
cctgggcagg gtctcgagtg gatgggcatt atcaatccgc atggtggcga tacgaagtac    180
gcgcagaagt ttcagggccg ggtgaccatg acccgtgata ccagcattag caccgcgtat    240
atggaactga gcagcctgcg tagcgaagat acggccgtgt attattgcgc gcgttggcat    300
catggtactt ggattttttga ttattggggc caaggcaccc tggtgacggt tagctca      357

<210> SEQ ID NO 31
<211> LENGTH: 360
<212> TYPE: DNA
<213> ORGANISM: Homo sapiens

<400> SEQUENCE: 31
caggtggaat tggttcagag cggcgcggaa gtgaaaaaac cgggcgaaag cctgaaaatt      60
agctgcaaag gttccggata ttcctttact tcttattgga ttggttgggt gcgccaggcc    120
cctgggaagg gtctcgagtg gatgggcatt atcgatccgg gtgatagccg tacccgttat    180
tctccgagct ttcagggcca ggtgaccatt agcgcggata aaagcattag caccgcgtat    240
cttcaatgga gcagcctgaa agcgagcgat acggccatgt attattgcgc gcgtggtcag    300
ctttatggtg gtacttatat ggatggttgg ggccaaggca ccctggtgac ggttagctca    360

<210> SEQ ID NO 32
<211> LENGTH: 330
```

```
<212> TYPE: DNA
<213> ORGANISM: Homo sapiens

<400> SEQUENCE: 32
gatatcgtgc tgacccagag cccggcgacc ctgagcctgt ctccgggcga acgtgcgacc      60
ctgagctgca gagcgagcca gtctgttcgt tcttctcgtc tggcttggta ccagcagaaa     120
ccaggtcaag caccgcgtct attaatttat ggtgcttcta agcgtgcaac tggggtcccg     180
gcgcgtttta gcggctctgg atccggcacg gattttaccc tgaccattag cagcctggaa     240
cctgaagact ttgcgactta ttattgccag cagtattatg attttcctcc tacctttggc     300
cagggtacga aagttgaaat taaacgtacg                                      330

<210> SEQ ID NO 33
<211> LENGTH: 333
<212> TYPE: DNA
<213> ORGANISM: Homo sapiens

<400> SEQUENCE: 33
gatatcgtgc tgacccagag cccggcgacc ctgagcctgt ctccgggcga acgtgcgacc      60
ctgagctgca gagcgagcca gtctgttcgt tcttctcgtc tggcttggta ccagcagaaa     120
ccaggtcaag caccgcgtct attaatttat ggtgcttcta agcgtgcaac tggggtcccg     180
gcgcgtttta gcggctctgg atccggcacg gattttaccc tgaccattag cagcctggaa     240
cctgaagact ttgcggtgta ttattgccag cagtattctc atgatccttc tggtaccttt     300
ggccagggta cgaaagttga aattaaacgt acg                                  333

<210> SEQ ID NO 34
<211> LENGTH: 333
<212> TYPE: DNA
<213> ORGANISM: Homo sapiens

<400> SEQUENCE: 34
gatatcgtgc tgacccagcc gccttcagtg agtggcgcac caggtcagcg tgtgaccatc      60
tcgtgtagcg gcagcagcag caacattggt tctaattatg tgtcttggta ccagcagttg     120
cccgggacgg cgccgaaact tctgatttat aatgataatc agcgtccctc aggcgtgccg     180
gatcgtttta gcggatccaa aagcggcacc agcgcgagcc ttgcgattac gggcctgcaa     240
agcgaagacg aagcggatta ttattgctct acttatgatc gtcgtacttt ttctgtgttt     300
ggcggcggca cgaagttaac cgtcctaggt cag                                  333

<210> SEQ ID NO 35
<211> LENGTH: 339
<212> TYPE: DNA
<213> ORGANISM: Homo sapiens

<400> SEQUENCE: 35
gatatcgcac tgacccagcc agcttcagtg agcggctcac caggtcagag cattaccatc      60
tcgtgtacgg gtactagcag cgatgttggt ggttataatt atgtgtcttg gtaccagcag     120
catcccggga aggcgccgaa acttatgatt tattctgttt ctaagcgtcc ctcaggcgtg     180
agcaaccgtt ttagcggatc caaaagcggc aacaccgcga gcctgaccat tagcggcctg     240
caagcggaag acgaagcgga ttattattgc gctacttggg atcattctca gatgggtaag     300
gtgtttggcg gcggcacgaa gttaaccgtc ctaggtcag                            339

<210> SEQ ID NO 36
```

```
<211> LENGTH: 327
<212> TYPE: PRT
<213> ORGANISM: Homo sapiens

<400> SEQUENCE: 36

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Val Ala Thr Leu Ile Asp Arg Phe Val Lys Gly Arg Gly
        115                 120                 125

Gln Leu Asp Lys Asp Thr Leu Asp Thr Leu Thr Ala Phe Tyr Pro Gly
    130                 135                 140

Tyr Leu Cys Ser Leu Ser Pro Glu Glu Leu Ser Ser Val Pro Pro Ser
145                 150                 155                 160

Ser Ile Trp Ala Val Arg Pro Gln Asp Leu Asp Thr Cys Asp Pro Arg
                165                 170                 175

Gln Leu Asp Val Leu Tyr Pro Lys Ala Arg Leu Ala Phe Gln Asn Met
            180                 185                 190

Asn Gly Ser Glu Tyr Phe Val Lys Ile Gln Ser Phe Leu Gly Gly Ala
        195                 200                 205

Pro Thr Glu Asp Leu Lys Ala Leu Ser Gln Gln Asn Val Ser Met Asp
    210                 215                 220

Leu Ala Thr Phe Met Lys Leu Arg Thr Asp Ala Val Leu Pro Leu Thr
225                 230                 235                 240

Val Ala Glu Val Gln Lys Leu Leu Gly Pro His Val Glu Gly Leu Lys
                245                 250                 255

Ala Glu Glu Arg His Arg Pro Val Arg Asp Trp Ile Leu Arg Gln Arg
            260                 265                 270

Gln Asp Asp Leu Asp Thr Leu Gly Leu Gly Leu Gln Gly Gly Ile Pro
        275                 280                 285

Asn Gly Tyr Leu Val Leu Asp Leu Ser Met Gln Glu Ala Leu Ser Gly
    290                 295                 300

Thr Pro Cys Leu Leu Gly Pro Gly Pro Val Leu Thr Val Leu Ala Leu
305                 310                 315                 320

Leu Leu Ala Ser Thr Leu Ala
                325
```

ANTI-MESOTHELIN IMMUNOCONJUGATES AND USES THEREFOR

CROSS REFERENCE TO RELATED APPLICATIONS

This application is a continuation application of U.S. patent application Ser. No. 14/803,410, filed Jul. 20, 2015, which is a continuation application of U.S. patent application Ser. No. 13/318,138, filed Jan. 18, 2012, now U.S. Pat. No. 9,084,829, which is the national stage of International Application No. PCT/EP2010/002342, filed internationally on Apr. 16, 2010, which claims the benefit of European Application No. 09005909.8, filed Apr. 29, 2009, the disclosures of which are hereby incorporated by reference in their entireties for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 777052009303SubSeqList.txt, date recorded: Mar. 30, 2018, size: 20 KB).

TECHNICAL FIELD

The present invention provides immunoconjugates comprising an antibody or fragment thereof, having specificity for the mesothelin protein, and a therapeutic agent. Compositions of such immunoconjugates can be used in treating, preventing, or diagnosing mesothelin-related disorders, e.g. cancer.

BACKGROUND ART

The occurrence of cancer is most commonly associated with aging whereby 65% of all new cases of cancer are recorded for patients aged 65 and over. Cancer is the second leading cause of death in the United States, exceeded only by heart disease. Indeed, the American Cancer Society has estimated that 1 in 4 people will die from cancer in the U.S., assuming current mortality rates remain static. In the U.S. alone, 1,437,180 new cases and 565,650 deaths from cancer are expected in 2008.

Antibody-based therapy is proving very effective in the treatment of various cancers, including solid tumors. For example, HERCEPTIN® has been used successfully to treat breast cancer. Central to the development of a successful antibody-based therapy is isolation of antibodies against cell-surface proteins found to be preferentially expressed on tumor cells. The mesothelin precursor polypeptide is a glycophosphatidylinositol (GPI)-anchored, glycosylated cell surface protein that is proteolytically cleaved to a 30 kDa N-terminal secreted polypeptide and a 40 kDa, C-terminal polypeptide, which predominantly occurs in the membrane-bound, GPI-anchored form (Chang, K. and I. Pastan, Proc. Natl. Acad. Sci. USA, (1996) 93(1):136), and which is named mesothelin herein. Mesothelin is preferentially expressed by certain tumor cells, particularly mesothelioma cells, pancreatic tumor cells and ovarian carcinoma cells, while its expression is limited in normal tissue, making it an attractive target for the development of tumor therapy (Argani, P. et al., Clin. Cancer Res. (2001) 7(12): 3862; Hassan, R., et al., Clin. Cancer Res. (2004) 10(12 Pt 1):3937). The function of mesothelin is unknown, and no apparent reproductive, hematologic, or anatomic abnormalities were observed in mice deficient in mesothelin gene expression (Bera, T. K. and I. Pastan, Mol. Cell. Biol. (2000) 20(8): 2902).

Antibody-based, targeted therapy against mesothelin-expressing cancer cells has been proposed for the treatment of lung, ovarian and pancreatic cancer. Mab K1 was the first antibody to membrane-bound mesothelin polypeptide which was described (Chang, K., et al., Int. J. Cancer, (1992) 50(3):373). Mab K1 was generated by immunizing mice. Due to low affinity and poor internalization rates of the antibody, an immunotoxin consisting of Mab K1 linked to a chemically modified truncated form of Pseudomonas exotoxin A was not considered suitable for clinical development (Hassan, R., et al., J. Immunother. (2000) 23(4):473; Hassan, R., et al., Clin. Cancer Res. (2004) 10(12 Pt 1): 3937). Subsequently, single-chain antibodies with higher affinities were developed, including SS1-(dsFv)-PE38, which showed killing activity of tumor cells in vitro (Hassan, R., et al., Clin. Cancer Res. (2002) 8(11): 3520) as well as potency in a murine model of human mesothelin-expressing tumors (Fan, D., et al., Mol. Cancer Ther. (2002) 1(8): 595). These data validate mesothelin as an attractive target to develop immunotherapy for the treatment of multiple cancers. SS1-(dsFv)-PE38 has been shown to have a fast blood clearance and attempts are being reported to increase the molecular weight by pegylating the fusion protein (Filpula, D., et al., Bioconjugate Chem. (2007) 18(3): 773).

MS-1, MS-2 and MS-3 are mesothelin-binding antibodies which elicit immune effector activity at the cell surface due to their human IgG1 isotype and internalize into mesothelin expressing cells (WO 2006/099141 A2). One of these antibodies, the unconjugated, chimeric (mouse/man) IgG1 anti-mesothelin antibody MORAb 009 is currently being tested in a clinical trial for therapeutic effects in the treatment of pancreatic cancer. The postulated mechanism of action of MORAb 009 is triggering of immune effector functions such as ADCC and function blocking. New therapies with inproved potency to fight aggressive cancers such as ovarian, pancreatic and lung cancer are highly desirable and would represent an advancement in the art. As such, the present invention discloses new immunoconjugate compositions that are useful in the treatment, prevention and/or diagnosis of mesothelin-related disorders, e.g. cancer.

SUMMARY OF THE INVENTION

The present invention relates to immunoconjugates comprising of antibodies, e.g., monoclonal antibodies, or fragments thereof that bind to mesothelin, that are conjugated to cytotoxic agents, e.g., maytansinoids, or derivatives thereof, and/or are co-administered or formulated with one or more additional anti-cancer agents. The immunoconjugates of the invention can be used to treat and/or diagnose and/or monitor mesothelin-related disorders, e.g. cancer.

It is an object of the invention to provide immunoconjugates comprising of antibodies, or antigen-binding antibody fragments thereof, or variants thereof, that are highly selective for the 40 kDa, C-terminal extracellular part of the mesothelin precursor polypeptide, and do bind mesothelin in the presence of cancer antigen 125 (CA125; MUC16), and an effector moiety. The particular properties of mesothelin antibodies have been described in PCT/EP2008/009756, and in one aspect of the invention, the combination of their particular ability to specifically immunoreact with mesothelin in the presence of CA125 in combination with a cytotoxic agent, e.g. maytansinoid, conjugation provides improved efficacy over function blocking antibodies, which compete with CA125 for mesothelin binding.

In one aspect, the antibodies, or fragments thereof of the invention are IgG antibodies or IgG fragments. The antibodies or fragments can also be IgG1, IgG2a, IgG2b, IgG3, IgM, IgD, IgE, IgA, or IgM antibodies, Fab fragments, F(ab')2 fragments, scFv fragments, Fv fragments, a diabodies, linear antibodies, single-chain antibodies, biospecific antibodies, multispecific antibodies, or chimeric antibodies (e.g. comprising a human antibody scaffold grafted to a human or non-human antibody binding region, or a non-human antibody scaffold grafted to a human or non-human antibody binding region). The chimeric antibodies can include, for example, antibody scaffold regions from non-human sources, such as, for example, cow, mouse, llama, camel, or rabbit. Further information on the engineering of antibodies can be found in the literature, for example, Holliger and Hudson, Nature Biotechnology, (September, 2005) 23: 1126-1136, which is incorporated herein by reference. The aforementioned fragments can be obtained from an immunoglobulin or produced by a suitable means, e.g. recombinant expression, in a fragment form.

The antibodies or antibody fragments of the invention can also be humanized, wherein the CDR sequences or regions (e.g. CDR1, CDR2, CDR3) can be non-human, e.g. murine.

The antibodies or antibody fragments of the invention, or compositions including the antibodies or fragments, can include a cytoxic agent that is conjugated to an antibody or fragment thereof. In one aspect, the cytotoxic agent is a maytansinoid or a dertivative thereof, however, other cytoxic agents are also provided, which can include, for example, and other cytotoxic agents, e.g., aplidin, auristatin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribomiclease, onconase, rapLR1, DNase I, Staphylococcal enterotoxin-A, pokeweed antiviral protein, gelonin, diphtheria toxin, or combinations thereof. Any of the cytoxic agents can also include functional analogs thereof or derivatives thereof.

In another aspect, the present invention provides immunoconjugates in which the cytotoxic agent is non-immunogenic, i.e. does not increase the immunogenicity of the parental antibody by contributing human or mammalian B cell epitopes or T cell epitopes to a drug formulation.

The compositions of the invention can include in addition to the antibodies and fragments (with or without the aforementioned conjugated cytoxic agents) various anticancer agents, which can include, for example, bleomycin, docetaxel (Taxotere), doxorubicin, edatrexate, erlotinib (Tarceva), etoposide, finasteride (Proscar), flutamide (Eulexin), gemcitabine (Gemzar), genitinib (Lrresa), goserelin acetate (Zoladex), granisetron (Kytril), imatinib (Gleevec), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), Triapine, vincristine, and vinorelbine tartrate (Navelbine), or therapeutic antibodies or fragments thereof, or anti-angiogenic agent, such as, for example, angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-IO, Gro-β, thrombospondin, 2-methoxyoestradiol, proliferin-related protein, carboxiamidotriazole, CM1O1, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline.

The present invention further provides in another aspect a method for treating a mesothelin-related disorder by administering a therapeutically effective amount of the immunoconjugates of the invention, or the compositions of the invention which include the immunoconjugates of the invention. The mesothelin-related disorder can include, for example, cancer, such as, a solid tumor cancer. The solid tumor can be in or originating from the ovary, pancreas, respiratory tract, lung, colon, stomach, esophagus, cervix, liver, breast, head, and neck.

These and other embodiments are disclosed or are obvious from and encompassed by, the following Detailed Description.

DETAILED DESCRIPTION OF THE INVENTION

Figure 1A:
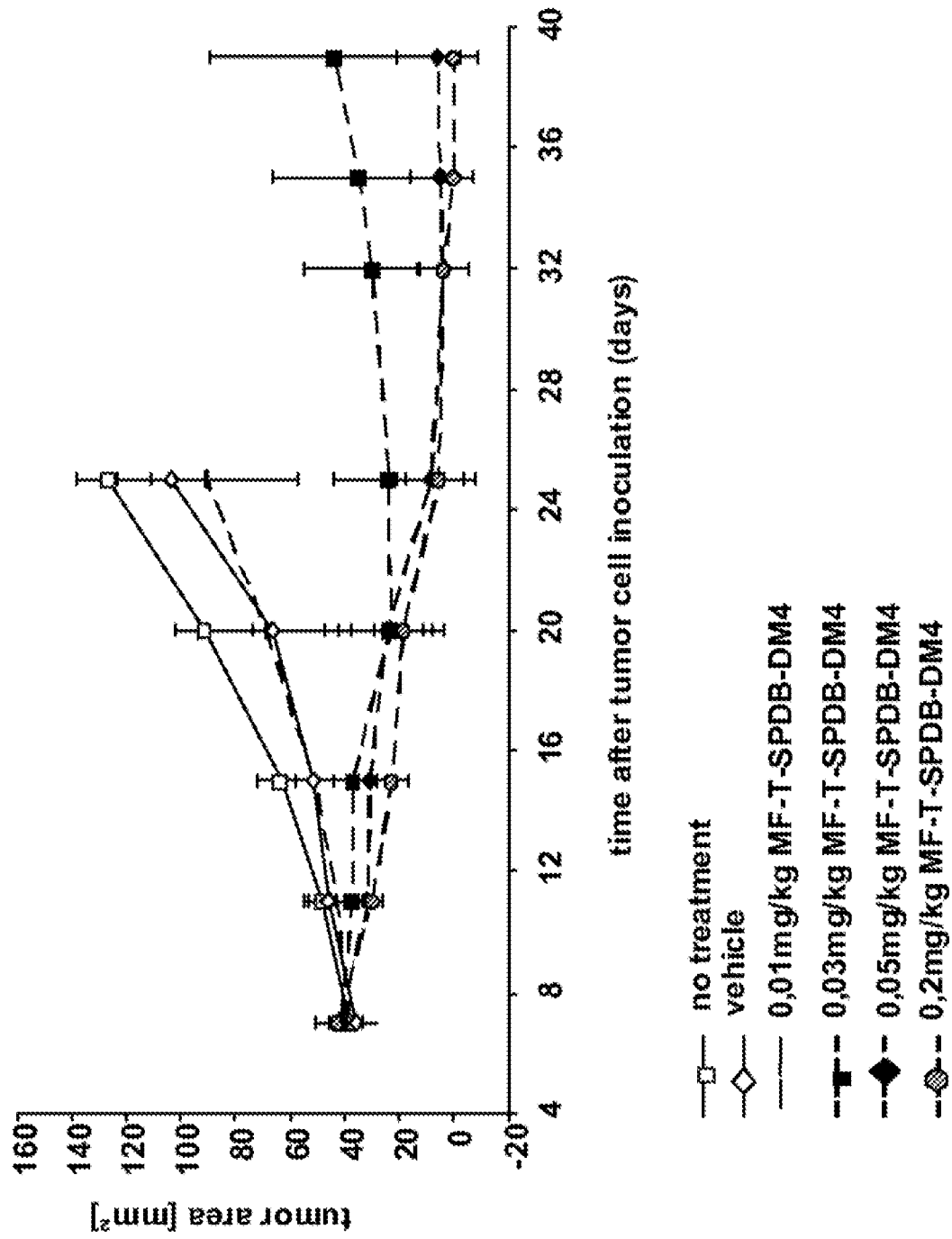
FIGS. 1A-B show anti-tumor efficacy of anti mesothelin-immunoconjugate MF-T-SPDB-DM4 on mesothelin-transfected human pancreas carcinoma cells in a mesothelin transfected xenograft model (FIG. 1A) as well as in non-transfected control tumors (FIG. 1B).

The present invention is based on the discovery of novel immunoconjugates that are specific to or have a high affinity for mesothelin and can deliver a therapeutic benefit to a subject. The immunoconjugates of the invention can be used in many contexts, which are more fully described herein. It is to be understood that present invention as described herein is not to be limited to the particular details set forth herein regarding any aspect of the invention, including, anti-mesothelin antibodies, immunoconjugates, methods of treatment, protocols, cell lines, animal species or genera, constructs, and reagents described, as such may vary. It is also to be understood that the terminology used herein is for the purpose of describing particular embodiments only, and is not intended to limit the scope of the present invention.

Definitions

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent the meaning commonly understood in the art. Such references include, but are not limited to, Singleton et ah, Dictionary of Microbiology and Molecular Biology (2d ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2nd Edition, W.B. Saunders Company. Any additional technical resources available to the person of ordinary skill in the art providing definitions of terms used herein having the meaning commonly understood in the art can be consulted. For the purposes of the present invention, the following terms are further defined. Additional terms are defined elsewhere in the description. As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

As used herein, the term "antibody" includes immunoglobulin molecules (e.g., any type, including IgG, IgE, IgM, IgD, IgA and IgY, and/or any class, including, IgG1, IgG2, IgG3, IgG4, IgA1 and Ig A2) isolated from nature or prepared by recombinant means. Antibodies also are meant to encompass antigen-binding antibody fragments, such as Fab, F(ab')2, scFv (single chain Fvs), Fv, single chain antibodies, diabodies, disulfide-linked Fvs (sdFv), and fragments comprising a VL or VH domain, which are prepared from intact immunoglobulins or prepared by recombinant means.

The antibodies and/or antigen-binding antibody fragments of the present invention may be monospecific (e.g. monoclonal), bispecific, trispecific or of greater multi specificity. Multispecific antibodies may be specific for different epitopes of an antigen or may be specific for epitopes of more than one antigen. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. ImmunoL 148:1547 1553, each of which are incorporated herein by reference.

Antigen-binding antibody fragments may comprise the variable region(s) alone or in combination with the entirety or a portion of the following: hinge region, CH1, CH2, CH3 and CL domains. Also included in the invention are antigen-binding antibody fragments also comprising any combination of variable region(s) with a hinge region, CH1, CH2, CH3 and CL domain.

Preferably, the antibodies or antigen-binding antibody fragments are human, humanized, murine (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. No. 5,939,598 by Kucherlapati et al. The term antibody also extends to other protein scaffolds that are able to orient antibody CDR inserts into the same active binding conformation as that found in natural antibodies such that binding of the target antigen observed with these chimeric proteins is maintained relative to the binding activity of the natural antibody from which the CDRs were derived. As used herein, the term "humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues (e.g. the complementarity determining regions "CDR") of the recipient are replaced by hypervariable region residues (CDRs) from a non-human species (donor antibody) such as mouse, rat, rabbit, or nonhuman primate having the desired specificity, affinity, and capacity. In some instances, framework region (FR) residues of the human immunoglobulin may be replaced by corresponding non-human residues. Furthermore, humanized antibodies may comprise residues which are not found in the recipient antibody or in the donor antibody. Such modifications are made to further refine antibody performance. In general, the humanized antibody may comprise substantially all of at least one or typically two variable domains, in which all or substantially all of the hypervariable regions correspond to those of a non-human immunoglobulin and all or substantially all of the FRs are those of a human immunoglobulin sequence. The humanized antibody optionally also may comprise at least a portion of an immunoglobulin constant region (Fc), typically that of a human immunoglobulin. For a review, see Jones, et al., (Nature 321:522-525, 1986); Reichmann, et al., (Nature 332:323-329, 1988); and Presta, (Curr. Op. Struct. Biol. 2:593-596, 1992). The preparation of humanized antibodies can be found in U.S. Pat. Nos. 7,049, 135, 6,828,422, 6,753,136, 6,706,484, 6,696,248, 6,692,935, 6,667,150, 6,653,068, 6,300,064, 6,294,353, and 5,514,548, each of which are incorporated herein in their entireties.

As used herein, the term "single-chain Fv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for antigen binding. For a review, see Pluckthun (The Pharmacology of Monoclonal Antibodies. Vol. 113, Rosenburg and Moore eds. Springer-Verlag, New York, pp. 269-315, 1994), which is incorporated herein in its entirety by reference.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger, et al., (Proc. Natl. Acad. Sci. USA 90:6444-6448, 1993), each of which are incorporated by reference.

The expression "linear antibodies" refers to the antibodies described in the art, for example, in Zapata, et al., (Protein Eng. 8(10): 1057-1062, 1995), which is incorporated by reference. Briefly, such antibodies comprise a pair of tandem Fd segments (VH-CHI-VH-CHI) which form a pair of antigen binding regions. Linear antibodies can be bispecific or monospecific.

The term "monoclonal antibody" as used herein refers to an antibody obtained from a population of substantially homogeneous antibodies, that is, individual antibodies comprising an identical population except for possible naturally occurring mutations that may be present in minor amounts. Monoclonal antibodies are highly specific, that is, directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., (Nature 256:495, 1975), or may be made by recombinant DNA methods {see, e.g., U.S. Pat. No. 4,816,567). Monoclonal antibodies may also be isolated from phage antibody libraries using the techniques described in, for example, Clackson, et al., (Nature 352:624-628,1991) and Marks, et al., (J. MoI. Biol. 222:581-597, 1991).

The monoclonal antibodies herein also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison, et al., Proc. Natl. Acad. Sci. USA 81:6851-6855, 1984, each of which are incorporated by reference).

As used herein, the terms "biological sample" or "patient sample" as used herein, refers to a sample obtained from an organism or from components (e.g., cells) of an organism. The sample may be of any biological tissue or fluid. The sample may be a "clinical sample" which is a sample derived from a patient. Such samples include, but are not limited to, sputum, blood, serum, plasma, blood cells (e.g., white cells), tissue samples, biopsy samples, urine, peritoneal fluid, and pleural fluid, saliva, semen, breast exudate, cerebrospinal fluid, tears, mucous, lymph, cytosols, ascites, amniotic fluid, bladder washes, and bronchioalveolar lavages or cells therefrom, among other body fluid samples. The patient samples may be fresh or frozen, and may be treated with heparin, citrate, or EDTA. Biological samples may also include sections of tissues such as frozen sections taken for histological purposes.

The term "cancer" includes, but is not limited to, solid tumors, such as cancers of the pancreas, breast, respiratory tract, brain, reproductive organs, digestive tract, urinary tract, eye, liver, skin, head and neck, thyroid, parathyroid, and their distant metastases. The term also includes sarcomas, lymphomas, leukemias, and plasma cell myelomas.

Tumors of the respiratory tract include, but are not limited to, small-cell and non-small-cell lung carcinoma, as well as bronchial adenoma and pleuropulmonary blastoma. Tumors of breast include, but are not limited to, invasive ductal carcinoma, invasive lobular carcinoma, ductal carcinoma in situ, and lobular carcinoma in situ. Tumors of brain include, but are not limited to, brain stem and hypophtalmic glioma, cerebellar and cerebral astrocytoma, medulloblastoma, ependymoma, as well as neuroectodermal and pineal tumor. Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus. Tumors of the digestive tract include, but are not limited to, anal, colon, colorectal, esophageal, gallbladder, gastric, pancreatic, rectal, small-intestine, and salivary gland cancers. Tumors of the urinary tract include, but are not limited to, bladder, penile, kidney, renal pelvis, ureter, and urethral cancers. Eye cancers include, but are not limited to, intraocular melanoma and retinoblastoma. Tumors of liver include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to, squamous cell carcinoma, Kaposi's sarcoma, malignant melanoma, Merkel cell skin cancer, and non-melanoma skin cancer. Head-and-neck cancers include, but are not limited to, laryngeal/hypopharyngeal/nasopharyngeal/oropharyngeal cancer, and lip and oral cavity cancer. Lymphomas include, but are not limited to, AIDS-related lymphoma, non-Hodgkin's lymphoma, cutaneous T-cell lymphoma, Hodgkin's disease, and lymphoma of the central nervous system. Sarcomas include, but are not limited to, sarcoma of the soft tissue, osteosarcoma, malignant fibrous histiocytoma, lymphosarcoma, and rhabdomyosarcoma. Leukemias include, but are not limited to, acute myeloid leukemia, acute lymphoblastic leukemia, chronic lymphocytic leukemia, chronic myelogenous leukemia, and hairy cell leukemia.

As used in this invention, the term "epitope" means any antigenic determinant on an antigen, e.g. mesothelin protein, to which the antibody binds through an antigenic binding site. Determinants or antigenic determinants usually consist of chemically active surface groupings of molecules such as amino acids or sugar side chains and usually have specific three dimensional structural characteristics, as well as specific charge characteristics.

The term "specifically immunoreactive" refers to a binding reaction between an antibody and a protein, compound, or antigen, having an epitope recognized by the antigenic binding site of the antibody. This binding reaction is determinative of the presence of a protein, antigen or epitope having the recognized epitope amongst the 10 presence of a heterogeneous population of proteins and other biologies. In the context of an immunoassay, specifically immunoreactive antibodies can bind to a protein having the recognized epitope and bind, if at all, to a detectably lesser degree to other proteins lacking the epitope which are present in the sample. In an in vivo context, "specifically immunoreactive" can refer to the conditions under which in an animal forms an immune response against a vaccine or antigen, e.g. a humoral response to the antigen (the production of antibodies, against a vaccine, protein, compound, or antigen presented thereto under immunologically reactive conditions)

or a cell-mediated (also herein as "cellular immune response", i.e. a response mediated by T lymphocytes against the vaccine, protein, compound or antigen presented thereto). As used herein, the term "immunologically reactive conditions" is used in the context of an immunoassay or an in vitro reaction wherein the physical conditions of the reaction, including, for example, the temperature, salt concentration, pH, reagents and their concentrations, and the concentrations of antigen and cognate antibody that is specifically immunoreactive to the antigen, are provided or adjusted to allow binding of the cognate antibody to the antigen. Immunologically reactive conditions are dependent upon the format of the antibody binding reaction and, typically are those utilized in immunoassay protocols. See Harlow and Lane (1988) Antibodies: A Laboratory Manual, Cold Spring Harbor Publications, New York, for a description of immunoassay formats and conditions. The term "patient" or "subject" as used herein includes mammals (e.g., humans and animals).

As used herein, the term 'invariant binding' of a particular antibody to mesothelin refers to its ability to bind to mesothelin on a broad range of mesothelin-expressing cancer cell lines which express different forms of mesothelin. Invariant binding may be caused by, but is not restricted to, the fact that antibodies, or antigen-binding antibody fragments thereof, or variants thereof, recognize an epitope of mesothelin that is not masked by another extracellular antigen, such as cancer antigen 125 (CA125), which interacts with mesothelin. For invariantly binding antibodies, EC50 values determined by FACS titration on two distinct cancer cell lines might differ no more than 10 fold, or, preferably, 5 fold, and most preferably between 1 and 3 fold.

As used herein, the term "immunoconjugate" refers to a conjugate molecule comprising at least one antibody or an antigen-binding fragment thereof, bound to a cytotoxic agent, e.g., a maytansinoid or a derivative thereof, preferably via a suitable linking group or a precursor thereof.

Immunoconjugates of the Invention

The present invention relates to methods to inhibit growth of mesothelin-positive cancer cells and the progression of neoplastic disease by providing anti-mesothelin immunoconjugates. The antibody moiety of the provided immunoconjugates are specifically immunoreactive to the 40 kDa, C-terminal domain of the mesothelin precursor polypeptide (SEQ ID NO 36), which is named 'mesothelin' herein.

In one aspect of the invention, the antibodies, antigen-binding antibody fragments, and variants of the antibodies and fragments of the invention have been described in PCT/EP2008/009756 and are comprised of a light chain variable region and a heavy chain variable region. Variants of the antibodies or antigen-binding antibody fragments contemplated in the invention are molecules in which the binding activity of the antibody or antigen-binding antibody fragment for mesothelin is maintained.

The present invention also relates to immunoconjugates composed of anti-mesothelin antibodies, antigen-binding antibody fragments, and variants of the antibodies and fragments of the invention different to those which have been described in (PCT/EP2008/009756), and linked to a chemotherapeutic agent, e.g. maytansinoids, or derivatives thereof.

Maytansinoids that can be used in the present invention are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:
(1) C-19-dechloro (U.S. Pat. No. 4,256,746) (prepared by LAH reduction of ansamitocin P2);
(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and
(3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:
(1) C-9-SH (U.S. Pat. No. 4,424,219) (prepared by the reaction of maytansinol with H2S or P2S5);
(2) C-14-alkoxymethyl (demethoxy/CH2OR) (U.S. Pat. No. 4,331,598);
(3) C-14-hydroxymethyl or acyloxymethyl (CH2OH or CH2OAc) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from *Trewia nudiflora*);
(6) C-18-N-demethyl (U.S. Pat. Nos. 4,362,663 and 4,322,348) (prepared by the demethylation of maytansinol by *Streptomyces*); and
(7) 4,5-deoxy (U.S. Pat. No. 4,371,533) (prepared by the titanium trichloride/LAH reduction of maytansinol).

The synthesis of thiol-containing maytansinoids useful in the present invention is fully disclosed in U.S. Pat. Nos. 5,208,020, 5,416,064, and 7,276,497.

Maytansinoids with a thiol moiety at the C-3 position, the C-14 position, the C-15 position or the C-20 position are all expected to be useful. The C-3 position is preferred and the C-3 position of maytansinol is especially preferred. Also preferred are an N-methyl-alanine-containing C-3 thiol moiety maytansinoid, and an N-methyl-cysteine-containing C-3 thiol moiety maytansinoid, and analogues of each. Preferred maytansinoids are those described in U.S. Pat. Nos. 5,208,020; 5,416,064; 6,333.410; 6,441,163; 6,716,821; RE39,151 and 7,276,497, each of which is incorporated herein in their entirety by reference. In a preferred embodiment, the esterified maytansinol is selected from N2'-deacetyl-N2'-(3-mercapto-1-oxopropyl)-maytansine (DM1, CAS Reg. No. 139504-50-0), N2'-deacetyl-N2'-(4-mercapto-1-oxopentyl)-maytansine (DM3, CAS Reg. No 796073-54-6), and N2'-deacetyl-N2'-(4-methyl-4-mercapto-1-oxopentyl)-maytansine (DM4 CAS Reg. No. 796073-69-3).

Throughout this document, reference is made to the following representative antibodies of the invention: "MF-J", "MOR06640", "MF-226", and "MF-T". MF-J represents an antibody having a variable heavy region corresponding to SEQ ID NO: 28 (DNA)/SEQ ID NO: 20 (protein) and a variable light region corresponding to SEQ ID NO: 32 (DNA)/SEQ ID NO: 24 (protein). MOR 06640 represents an antibody having a variable heavy region corresponding to SEQ ID NO: 29 (DNA)/SEQ ID NO: 21 (protein) and a variable light region corresponding to SEQ ID NO: 33 (DNA)/SEQ ID NO: 25 (protein). MF-226 represents an antibody having a variable heavy region corresponding to SEQ ID NO: 30 (DNA)/SEQ ID NO: 22 (protein) and a variable light region corresponding to SEQ ID NO: 34 (DNA)/SEQ ID NO: 26 (protein). MF-T represents an antibody having a variable heavy region corresponding to SEQ ID NO: 31 (DNA)/SEQ ID NO: 23 (protein) and a variable light region corresponding to SEQ ID NO: 35 (DNA)/SEQ ID NO: 27 (protein). The invention is not limited to these antibodies which are used here as are examples. Other usefull antibodies are disclosed for example in PCT/EP2008/009756.

In one aspect, the invention provides immunoconjugates that are specifically immunoreactive to mesothelin in the presence of cancer antigen 125 (CA 125/MUC 16), and therefore efficiently target cancer cells expressing both mesothelin and CA125, e.g. OVCAR-3 cells.

In other aspects the invention provides immunoconjugates which are specifically immunoreactive to one or more amino acids of the epitopes of antibodies MOR 06640 or MF-T. In certain aspects said immunoconjugates are specifically immunoreactive to at least to two, at least three, at least four, at least five or at least six amino acids of the epitopes of antibodies MOR 06640 or MF-T. In certain aspects the immunoconjugates of the present invention are specifically immunoreactive to one or more amino acids of the epitope recognized by the antibody MOR 06640. In alternative aspects the antibodies of the present invention are specifically immunoreactive to one or more amino acids of the epitope recognized by the antibody MF-T.

In another aspect, the invention provides immunoconjugates having an antigen-binding region that is specifically immunoreactive to or has a high affinity for one or more regions of mesothelin, whose amino acid sequence is depicted by SEQ ID NO: 36. An immunoconjugate is said to have a "high affinity" for an antigen if the affinity measurement is at least 100 nM (monovalent affinity of Fab fragment). An inventive immunoconjugate preferably can be specifically immunoreactive to mesothelin with an affinity of less than about 100 nM, more preferably less than about 60 nM, and still more preferably less than about 30 nM. Further preferred are antibodies that bind to mesothelin with an affinity of less than about 10 nM, and more preferably less than about 3 nM. For instance, the affinity of an antibody of the invention against mesothelin may be about 9.1 nM or 0.9 nM (monovalent affinity of IgG1 format).

Methods of Use

The term "treatment" includes any process, action, application, therapy, or the like, wherein a subject (or patient), including a human being, is provided medical aid with the object of improving the subject's condition, directly or indirectly, or slowing the progression of a condition or—disorder in the subject, or ameliorating at least one symptom of the disease or disorder under treatment.

The term "combination therapy" or "co-therapy" means the administration of two or more therapeutic agents to treat a disease, condition, and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner. The order of administration of two or more sequentially co-administered therapeutic agents is not limited. The phrase "therapeutically effective amount" means the amount of each agent administered that will achieve the goal of improvement in a disease, condition, and/or disorder severity, and/or symptom thereof, while avoiding or minimizing adverse side effects associated with the given therapeutic treatment.

The term "pharmaceutically acceptable" means that the subject item is appropriate for use in a pharmaceutical product.

The immunoconjugates of this invention are expected to be valuable as therapeutic agents. Accordingly, an embodiment of this invention includes a method of treating the various conditions in a patient (including mammals) which comprises administering to said patient a composition containing an amount of an immunoconjugate of the invention that is effective in treating the target condition.

The immunoconjugates of the present invention may be used in the treatment or prevention of diseases and/or behaviors that are associated with the mesothelin protein. These diseases and/or behaviors include, for example, cancer, such as, carcinomas of the pancreas, ovary, stomach, esophagus, cervix, colon, liver, respiratory tract, and lung. The present invention also relates to methods of ameliorating symptoms of a disorder in which mesothelin is elevated or otherwise abnormally expressed. These disorders include, without limitation, carcinomas of the pancreas, ovary, stomach, esophagus, cervix, colon, liver, respiratory tract, and lung (see, e.g., (Liao, Cancer Res. 57:2827-2831, 1997; Turner, Hum. Pathol. 28:740-744, 1997; Liao, et al., Am. J. Pathol. 145:598-609, 1994; Saarnio, et al., Am. J. Pathol. 153:279-285, 1998; Vermylen, et al., Eur. Respir. J. 14:806-811, 1999). In one embodiment of the invention, a therapeutically effective dose of an immunoconjugate of the invention is administered to a patient having a disorder in which mesothelin is elevated.

Immunoconjugates of the present invention may be administered alone or in combination with one or more additional therapeutic agents. Combination therapy includes administration of a single pharmaceutical dosage formulation which contains an immunoconjugate of the present invention and one or more additional therapeutic agents, as well as administration of the immunoconjugate of the present invention and each additional therapeutic agents in its own separate pharmaceutical dosage formulation. For example, an immunoconjugate of the present invention and a therapeutic agent may be administered to the patient together in a single oral dosage composition or each agent may be administered in separate oral dosage formulations.

Where separate dosage formulations are used, the immunoconjugate of the present invention and one or more additional therapeutic agents may be administered at essentially the same time (e.g., concurrently) or at separately staggered times (e.g., sequentially). The order of administration of the agents is not limited.

For example, in one aspect, co-administration of an anti-mesothelin immunoconjugate of the invention together with one or more anti-cancer agents to potentiate the effect of either the anti-mesothelin immunoconjugate or the anti-cancer agent(s) or both is contemplated for use in treating mesothelin-related disorders, such as, cancer. Such combination-therapies may also be used to prevent cancer, prevent the recurrence of cancer, prevent the spread or metastasis of a cancer, or reduce or ameliorate the symptoms associated with cancer.

The one or more anti-cancer agents can include any known and suitable compound in the art, such as, for example, chemoagents, other immunotherapeutics, cancer vaccines, anti-angiogenic agents, cytokines, hormone therapies, gene therapies, and radiotherapies. A chemoagent (or "anti-cancer agent" or "anti-tumor agent" or "cancer therapeutic") refers to any molecule or compound that assists in the treatment of a cancer. Examples of chemoagents contemplated by the present invention include, but are not limited to, cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cyt-arabine, flavopiridol, 5-fluorouracil, fludarabine, gemcitabine, dacarbazine, temozolamide), asparaginase, Bacillus Calmette and Guerin, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, vinca alkyloids such as vinblastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, *pseudomonas* exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamyein, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

The chemoagent can be an anti-angiogenic agent, such as, for example, angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Fit-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM1O1, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline.

In one aspect, said chemoagent is gemcitabine at a dose ranging from 100 to 1000 mg/m2/cycle. In one embodiment, said chemoagent is dacarbazine at a dose ranging from 200 to 4000 mg/m2 cycle. In another aspect, said dose ranges from 700 to 1000 mg/m2/cycle. In yet another aspect, said chemoagent is fludarabine at a dose ranging from 25 to 50 mg/m2/cycle. In another aspect, said chemoagent is cytosine arabinoside (Ara-C) at a dose ranging from 200 to 2000 mg/m2/cycle. In still another aspect, said chemoagent is docetaxel at a dose ranging from 1.5 to 7.5 mg/kg/cycle. In yet another aspect, said chemoagent is paclitaxel at a dose ranging from 5 to 15 mg/kg/cycle. In a further aspect, said chemoagent is cisplatin at a dose ranging from 5 to 20 mg/kg/cycle. In a still further aspect, said chemoagent is 5-fluorouracil at a dose ranging from 5 to 20 mg/kg/cycle. In another aspect, said chemoagent is doxorubicin at a dose ranging from 2 to 8 mg/kg/cycle. In yet a further aspect, said chemoagent is epipodophyllotoxin at a dose ranging from 40 to 160 mg/kg/cycle. In yet another aspect, said chemoagent is cyclophosphamide at a dose ranging from 50 to 200 mg/kg/cycle. In a further aspect, said chemoagent is irinotecan at a dose ranging from 50 to 150 mg/m2/cycle. In a still further aspect, said chemoagent is vinblastine at a dose ranging from 3.7 to 18.5 mg/m2/cycle. In another aspect, said chemoagent is vincristine at a dose ranging from 0.7 to 2 mg/m2/cycle. In one aspect, said chemoagent is methotrexate at a dose ranging from 3.3 to 1000 mg/m/cycle.

In another aspect, the anti-mesothelin immunoconjugates of the present invention are administered in combination with one or more immunotherapeutic agents, such as antibodies or immunomodulators, which include, but are not limited to, Herceptin®, Retuxan®, OvaRex, Panorex, BEC2, IMC-C225, Vitaxin, Campath I/H, Smart MI95, LymphoCide, Smart I D 10, and Oncolym, rituxan, rituximab, gemtuzumab, or trastuzumab.

The invention also contemplates administering the anti-mesothelin immunoconjugates of the present invention with one or more anti-angiogenic agents, which includes, but is not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a β-amino acid peptide corresponding to a fragment of platelet factor-4 (Maione et al., 1990, Cancer Res. 51:2077), a 14-amino acid peptide corresponding to a fragment of collagen I (Tolma et al., 1993, J. Cell Biol. 122:497), a 19 amino acid peptide corresponding to a fragment of Thrombospondin I (Tolsma et al., 1993, J. Cell Biol. 122:497), a 20-amino acid peptide corresponding to a fragment of SPARC (Sage et al., 1995, J. Cell. Biochem. 57: 1329-), or any fragments, family members, or derivatives thereof, including pharmaceutically acceptable salts thereof. Other peptides that inhibit angiogenesis and correspond to fragments of laminin, fibronectin, procollagen, and EGF have also been described (See the review by Cao, 1998, Prog. Mol. Subcell. Biol. 20:161). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569; Hammes et al., 1996, Nature Medicine 2:529). Moreover, inhibition of the urokinase plasminogen activator receptor by antagonists inhibits angiogenesis, tumor growth and metastasis (Min et al., 1996, Cancer Res. 56:2428-33; Crowley et aL, 1993, Proc Natl Acad. Sci. USA 90:5021). Use of such anti-angiogenic agents is also contemplated by the present invention.

In another-aspect, the anti-mesothelin immunoconjugates of the present invention are administered in combination with a regimen of radiation.

The anti-mesothelin immunoconjugates of the present invention can also be administered in combination with one or more cytokines, which includes, but is not limited to, lymphokines, tumor necrosis factors, tumor necrosis factor-like cytokines, lymphotoxin-α, lymphotoxin-β, interferon- β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD 137 ligands, Fas-Pas ligand, 4-IBBL, endothelial monocyte activating protein or any fragments, family members, or derivatives thereof, including pharmaceutically acceptable salts thereof.

The anti-mesothelin immunoconjugates of the present invention can also be administered in combination with a cancer vaccine, examples of which include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gplOO, MART-1/MelanA, TRP-I (gp75), tyrosinase, widely shared tumor-associated, including tumor-specific, antigens (e.g., BAGE, GAGE-I, GAGE-2, MAGE-I, MAGE-3, N-acetylglucosaminyltransferase-V, p15), mutated antigens that are tumor-associated (β-catenin, MUM-I, CDK4), nonmelanoma antigens (e.g., HER-2/neu (breast and ovarian carcinoma), human 5 papillomavirus-E6, E7 (cervical carcinoma), MUC-1 (breast, ovarian and pancreatic carcinoma). For human tumor antigens recognized by T-cells, see generally Robbins and Kawakami, 1996, Curr. Opin. Immunol. 8:628. Cancer vaccines may or may not be purified preparations.

In yet another embodiment, the anti-mesothelin immunoconjugates of the present invention are used in association with a hormonal treatment. Hormonal therapeutic treatments comprise hormonal agonists, hormonal antagonists (e.g., flutamide, tamoxifen, leuprolide acetate (LUPRON), LH-RH antagonists), inhibitors of hormone biosynthesis and processing, and steroids (e.g., dexamethasone, retinoids, betamethasone, Cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

The anti-mesothelin immunoconjugates of the invention can be used in combination with, e.g. co-administered with, an anti-MDR (multidrug resistance) phenotype agent. Many human cancers intrinsically express or spontaneously develop resistance to several classes of anticancer drugs at the same time, notwithstanding that each of the drug classes have different structures and mechanisms of action. This phenomenon, which can be mimicked in cultured mammalian cells, is generally referred to as multidrug resistance ("MDR") or the multidrug resistance phenotype. The MDR phenotype presents significant obstacles to the successful chemotherapeutic treatments for cancers in human patients. Resistance of malignant tumors to multiple chemotherapeutic agents is a major cause of treatment failure (Wines et al., Cancer Treat. Rep. 70:105 (1986); Bradley, G. et al., Biochim. Biophys. Acta 948:87 (1988); Griswald, D. P. et al., Cancer Treat. Rep. 65(52):51 (1981); Osteen, R. T. (ed.), Cancer Manual, (1990)). Tumors initially sensitive to cytotoxic agents often recur or become refractory to multiple chemotherapeutic drugs (Riordan et al., Pharmacol. Ther. 28:51 (1985); Gottesman et al., Trends Pharmacol. Sci. 9:54 (1988); Moscow et al., J. Natl. Cancer Inst. 80:14 (1988); Croop, J. M. et al., J. Clin. Invest. 81:1303 (1988)). Cells or tissues obtained from tumors and grown in the presence of a selecting cytotoxic drug can result in cross-resistance to other drugs in that class as well as other classes of drugs including, but not limited to, anthracyclines, Vinca alkaloids, and epipodophyllotoxins (Riordan et al., Pharmacol. Ther. 28:51 (1985); Gottesman et al., J. Biol. Chem. 263: 12163 (1988)). Thus, acquired resistance to a single drug results in simultaneous resistance to a diverse group of drugs that are structurally and functionally unrelated. Such resistance can be a problem for both solid-form and liquid-form tumors (e.g. blood or lymph-based cancers).

One major mechanism of multidrug resistance in mammalian cells involves the increased expression of the 170 kDa plasma membrane glycoprotein pump system (Juranka et al., FASEB J 3:2583 (1989); Bradley, G. et al., Biochem. Biophys. Acta 948:87 (1988)). The gene encoding this pump system, sometimes referred to as a multidrug transporter, has been cloned from cultured human cells and is generally referred to as mdrl. This gene is expressed in several classes of normal tissues, but physiological substrates transported for the mdrl gene product in these tissues have not been identified. The MDRl product is a member of the ABC Transporter Protein superfamily, a group of proteins having energy-dependent export function. The protein product of the mdrl gene, generally known as P-glycoprotein ("P-170", "P-gp"), is a 170 kDa trans-plasma membrane protein that constitutes the aforementioned energy-dependent efflux pump. Expression of P-gp on the cell surface is sufficient to render cells resistant to multiple cytotoxic drugs, including many anti-cancer agents. P-gp-mediated MDR appears to be an important clinical component of tumor resistance in tumors of different types, and mdrl gene expression correlates with resistance to chemotherapy in different types of cancer. The nucleotide sequence of the mdrl gene (Gros, P. et al., Cell 47:371 (1986); Chen, C. et al., Cell 47:381 (1986)) indicates that it encodes a polypeptide similar or identical to P-glycoprotein and that these are members of the highly conserved class of membrane proteins similar to bacterial transporters and involved in normal physiological transport processes. Sequence analysis of the mdrl gene indicates that Pgp consists of 1280 amino acids distributed between two homologous (43% identity) halves. Each half of the molecule has six hydrophobic transmembrane domains and each has an ATP binding site within the large cytoplasmic loops. Only about 8% of the molecule is extracellular, and the carbohydrate moiety (approximately 30 kDa) is bound to sites in this region.

Thus, it will be appreciated that mammalian cells having a "multidrug-resistance" or "multidrug-resistant" phenotype are characterized by the ability to sequester, export or expel a plurality of cytotoxic substances (e.g., chemotherapeutic drugs) from the intracellular milieu. Cells may acquire this phenotype as a result of selection pressure imposed by exposure to a single chemotherapeutic drug (the selection toxin). Alternatively, cells may exhibit the phenotype prior to toxin exposure, since the export of cytotoxic substances may involve a mechanism in common with normal export of cellular secretion products, metabolites, and the like. Multidrug resistance differs from simple acquired resistance to the selection toxin in that the cell acquires competence to export additional cytotoxins (other chemotherapeutic drugs) to which the cell was not previously exposed. For example, Mirski et al. (1987), 47 Cancer Res. 2594-2598, describe the isolation of a multidrug-resistant cell population by culturing the H69 cell line, derived from a human small cell lung carcinoma, in the presence of adriamycin (doxorubicin) as a selection toxin. Surviving cells were found to resist the cytotoxic effects of anthracycline analogs (e.g., daunomycin, epirubicin, menogaril and mitoxantrone), acivicin, etoposide, gramicidin D, colchicine and Vinca-derived alkaloids (vincristine and vinblastine) as well as of adriamycin. Similar selection culturing techniques can be applied to generate additional multidrug-resistant cell populations. Accordingly, the pharmaceutical compositions of the invention can additionally include compounds which act to inhibit the MDR phenotype and/or conditions associated with MDR phenotype. Such compounds can include any known MDR inhibitor compounds in the art, such as, antibodies specific for MDR components (e.g. anti-MDR transporter antibodies) or small molecule inhibitors of MDR transporters, including specifically, tamoxifen, verapamil and cyclosporin A, which are agents known to reverse or inhibit multidrug resistance. (Lavie et al. J. Biol. Chem. 271: 19530-10536, 1996, incorporated herein by reference). Such compounds can be found in U.S. Pat. Nos. 5,773,280, 6,225,325, and 5,403,574, each of which are incorporated herein by reference. Such MDR inhibitor compounds can be co-administered with the anti-mesothelin immunoconjugates of the invention for various purposes, including, reversing the MDR phenotype following the detection of the MDR phenotype to assist or enhance a chemotherapeutic treatment. The MDR inhibitor, such as, for example, tamoxifen, verapamil or cyclosporin A, may be used in conjuction with the compounds of the invention to assist in the detection of the MDR phenotype. In accordance with this aspect, an MDR inhibitor can enhance the uptake and accumulation of a compound of the invention in an MDR cancer cell since the capacity of the MDR transport system in transporting or "pumping out" the imaging compound vis-a-vis the substrate domain would be diminished in the presence of an MDR inhibitor.

In yet another embodiment, the anti-mesothelin immunoconjugates of the present invention are used in association with a gene therapy program in the treatment of cancer. Gene therapy with recombinant cells secreting interleukin-2 can be administered in combination with the inventive immunoconjugates to prevent or treat cancer, particularly breast cancer (See, e.g., Deshmukh et ah, 2001, J. Neurosurg. 94:287).

To assess the ability of a particular immunoconjugate to be therapeutically useful to treat cancer, as an example, the immunoconjugate may be tested in vivo in a mouse xenograft tumor model. Examples of therapeutic models are detailed in Examples 1 and 2. Antibody activity may also be tested using an antibody dependent cell-mediated cytotoxicity assay as described in Example 3.

Pharmaceutical Compositions and Dosages

The immunoconjugates described herein may be provided in a pharmaceutical composition comprising a pharmaceutically acceptable carrier. The pharmaceutically acceptable carrier may be non-pyrogenic. The compositions may be administered alone or in combination with at least one other agent, such as stabilizing compound, which may be administered in any sterile, biocompatible pharmaceutical carrier including, but not limited to, saline, buffered saline, dextrose, and water. A variety of aqueous carriers may be employed including, but not limited to saline, glycine, or the like. These solutions are sterile and generally free of particulate matter. These solutions may be sterilized by conventional, well-known sterilization techniques (e.g., filtration).

Generally, the phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other nontoxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the immunoconjugate compositions of the invention.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions may contain pharmaceutically acceptable auxiliary substances as required to approximate physiological conditions such as pH adjusting and buffering agents, and the like. The concentration of the immunoconjugate of the invention in such pharmaceutical formulation may vary widely, and may be selected primarily based on fluid volumes, viscosities, etc., according to the particular mode of administration selected. If desired, more than one type of antibody or immunoconjugate may be included in a pharmaceutical composition (e.g., an antibody with different Ka for mesothelin binding).

The compositions may be administered to a patient alone, or in combination with other agents, drugs or hormones. In addition to the active ingredients, these pharmaceutical compositions may contain suitable pharmaceutically acceptable carriers comprising excipients and auxiliaries that facilitate processing of the active compounds into preparations which may be used pharmaceutically. Pharmaceutical compositions of the invention may be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

The compositions of the invention additionally contemplate suitable immunocarriers, such as, proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein-derived or non-protein derived substances are known to those skilled in the art.

In aspects involving vaccines, e.g. cancer vaccines together with the antibodies of the invention, the compositions of the invention can be administered with or without an adjuvant. Administration can be carried out in the absence of an adjuvant in order to avoid any adjuvant-induced toxicity. The person of ordinary skill in the art to which this invention pertains, e.g. a medical doctor specializing in cancer, will appreciate and understand how to ascertain whether an adjuvant should or should not be used and can dependent upon the medical history of a subject, family data, toxicity data, allergy-related test results, etc. In embodiments where an adjuvant is used, it is advantageous that the adjuvant promotes the formation of protective antibodies, such as protective IgG antibodies. Any suitable adjuvant known to one of ordinary skill in the art is contemplated by the present invention and are readily adapted to this invention. Suitable adjuvants for use in vaccinating animals can include, but are not limited to, aluminum hydroxide, saponin-and-its purified component Quit A, complete Freund's adjuvant (CFA) and incomplete Freund's adjuvant (IFA). Dextran sulfate has been shown to be a potent stimulator of IgG2 antibody against staphylococcal cell surface antigens, and also is suitable as an adjuvant. It will be appreciated by the skilled person that some adjuvants can be more preferable for veterinary application, whereas other adjuvants will be preferable for use in humans, and that adjuvant toxicities are a consideration that should be made by the skilled person prior to administration of the compound to a human.

Formulations suitable for parenteral, subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20th edition, 2000). Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The determination of a therapeutically effective dose is well within the capability of those skilled in the art. A therapeutically effective dose refers to the amount of an immunoconjugate that may be used to effectively treat a disease (e.g., cancer) compared with the efficacy that is evident in the absence of the therapeutically effective dose.

The therapeutically effective dose may be estimated initially in animal models (e.g., rats, mice, rabbits, dogs, or pigs). The animal model may also be used to determine the appropriate concentration range and route of administration. Such information may then be used to determine useful doses and routes for administration in humans. Therapeutic efficacy and toxicity (e.g., ED50—the dose therapeutically effective in 50% of the population and LD50—the dose lethal to 50% of the population) of an immunoconjugate may be determined by standard pharmaceutical procedures in cell cultures or experimental animals. The dose ratio of toxic to therapeutic effects is the therapeutic index, and it may be expressed as the ratio, LD50/ED50. The data obtained from animal studies may used in formulating a range of dosage for human use. The dosage contained in such compositions may be within a range of circulating concentrations that include the ED50 with little or no toxicity. The dosage varies within this range depending upon the dosage form employed, sensitivity of the patient, and the route of administration.

The exact dosage may be determined by the practitioner, in light of factors related to the patient who requires treatment. Dosage and administration may be adjusted to provide sufficient levels of the immunoconjugate or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Polynucleotides encoding immunoconjugates of the invention may be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of toxophore components of an immunoconjugate are in the range of about 5 µg to about 500 µg/kg of patient body weight. The mode of administration of immunoconjugate-containing pharmaceutical compositions of the present invention may be any suitable route which delivers the antibody to the host. As an example, pharmaceutical compositions of the invention may be useful for parenteral administration (e.g., subcutaneous, intramuscular, intravenous, or intranasal administration). All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLES

Example 1: Immunoconjugate Efficacy in a Mesothelin Expressing Human Pancreatic Carcinoma Xenograft Mouse Model In order to analyse if the anti-mesothelin immunoconjugates were able to reduce the growth of tumors in a mesothelin dependent manner, human pancreatic carcinoma cells (MiaPaCa-2) were stably transfected with mesothelin and used to establish a subcutaneously growing tumor mouse model. The human colon carcinoma cell line HT29 was used to establish mesothelin negative control tumors within the efficacy study. MiaPaCa cells were maintained as adherent cultures in DMEM medium supplemented with 10% (v/v) FCS, 2.5% (v/v) horse serum, 1.5 g/l sodiumbicabonate, 4.5 g/l glucose, 4 mM glutamine and 0,4% (v/v) Hygromycin. HT29 cells were cultured in McCoy's 5a medium with 1.5 mM glutamine, 2.2 g/l sodiumbicarbonate and 10% (v/v) FCS. Mesothelin expression of MiaPaCa-2 cells and absence of mesothelin in HT29 cells was confirmed by FACS (not shown). To assess in vivo growth of the tumor cells, female NMRI nude mice were subcutaneously inoculated into the right flank with $3\times10^6$ MiaPaCa-2 cells or $1\times10^6$ HT29 cells, resuspended in 50% Matrigel™ and 50% Medium. As anti-mesothelin immunoconjugates MF-J-SPDB-DM4, MF-T-SPDB-DM4, MF226-SPDB-DM4 and MOR6640-SPDB-DM4 have been tested at treatment doses of 0.01 mg/kg, 0.03 mg/kg, 0.05 mg/kg and 0.2 mg/kg (related to the amount of toxophore). MF-J-SPDB-DM4, MF-T-SPDB-DM4, MF226-SPDB-DM4 and MOR6640-SPDB-DM4 were generated by the following procedure: Anti-mesothelin antibodies were modified with 4-[2-pyridyldithio]butanoic acid N-hydroxsuccinimide ester (SPDB) to introduce dithiopyridyl groups. At 8 mg/mL antibody, a ~6-fold molar excess of SPDB (~20 mM stock solution in EtOH) was used to modify the antibody. Modified antibodies were reacted with a 1.7-fold molar excess of the free thiol form of maytansinoid over thiopyridyl. The reaction was carried out at 2.5 mg/ml antibody in the presence of 3% dimethylacetamide (3% v/v) for 20 hours at room temperature. The conjugation reaction mixture was purified from unreacted drug and reaction byproducts using a desalting Sephadex G25 column. The number of maytansinoid molecules per antibody was calculated by measuring absorbances at 252 nm and at 280 nm, using extinction coefficients of 224000 $M^{-1}$ $cm^{-1}$ for antibody and 5180 $M^{-1}$ $cm^{-1}$ for DM4 at 280 nm. The 252 nm/280 nm absorbance ratio is 0.37 for antibody and 5.05 for DM4.

Figure 1B:
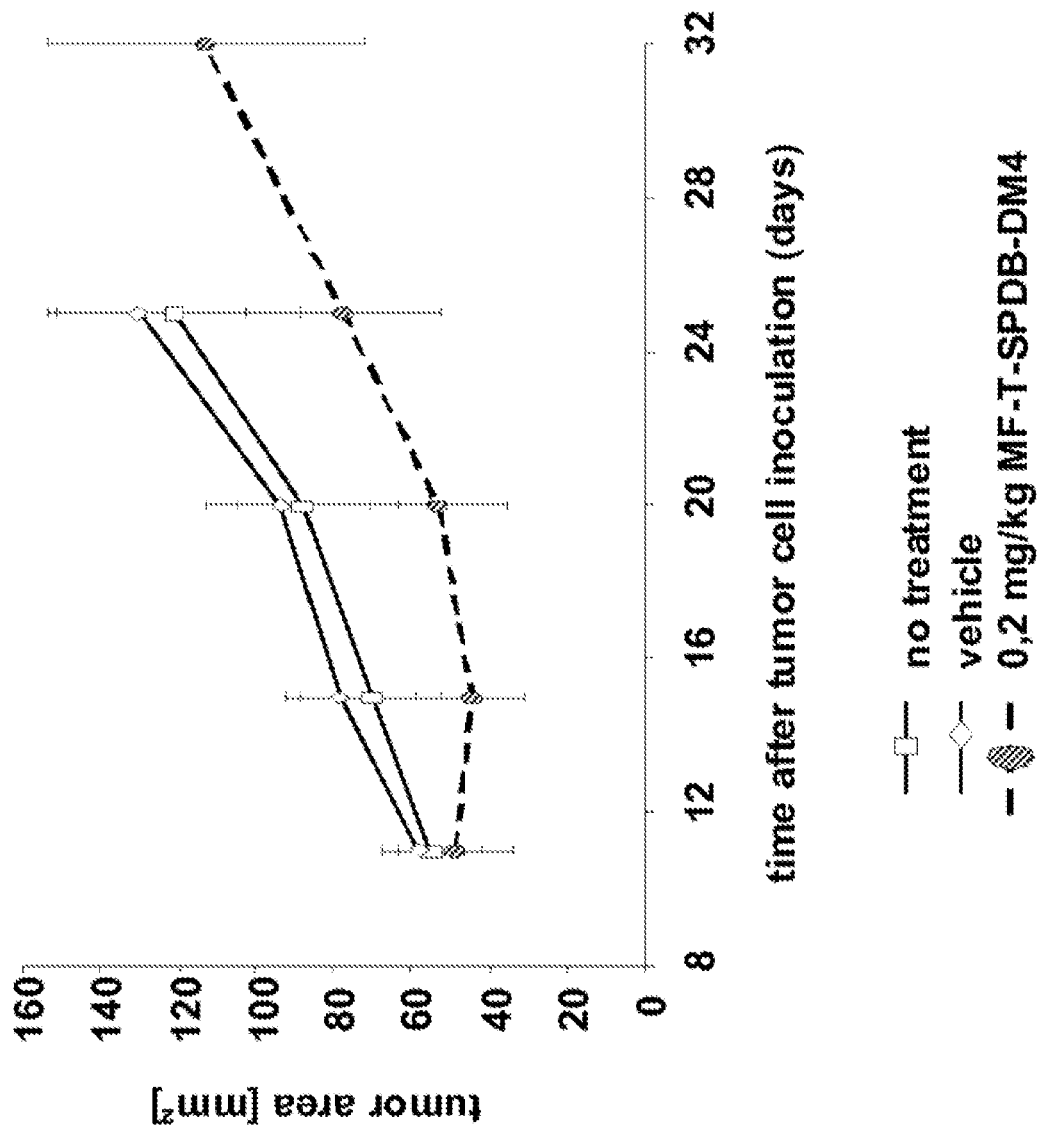

Treatment started after tumor establishment at day 5 after tumor cell inoculation, followed by two further treatments on days 8 and 12 after tumor cell inoculation. Control mice were either treated with 0.2 mg/kg of the non-targeting immunoconjugate (anti-lysozyme-SPDB-DM4) or with equal volumes of vehicle alone (10 mM histidine, 130 mM glycine, 5% (w/v) sucrose, pH 5.5). Treatments occurred with a dosage volume of 100 µl/10 g body weight via intravenous application. Groups consisted of 6 animals each. The health status of the mice was examined daily. Length and width of the subcutaneous tumors were measured using an electronic caliper twice per week. Tumor area was calculated by the formula: tumor area $[mm^2]$=length [mm]× width [mm]. All data obtained throughout the experiment were documented. An example of anti-tumor efficacy of anti mesothelin immunoconjugate MF-T-SPDB-DM4 on mesothelin-transfected human pancreas carcinoma cells at different treatment doses is shown in FIG. 1. Female NMRI nude mice were inoculated with $3\times10^6$ mesothelin positive MiaPaCa-2 human pancreas carcinoma cells (A) or $1\times10^6$ mesothelin negative HT29 human colon carcinoma cells (B) resuspended in 50% Matrigel™/50% medium into their right flank. 5, 8, and 12 days after tumor cell inoculation, mice received 0.01, 0.03, 0.05, 0.2 mg/kg MF-T-SPDB-DM4, (all concentrations relate to the amount of toxophore), or vehicle alone. Length and width of the tumors were measured twice per weak and tumor area was calculated by multiplication of width and length. Mean values and standard derivation for every group and measuring time point are plotted. All n=6. Asterisks indicate P-values<0.05.

The treatment of the tumor-bearing mice revealed that all anti-mesothelin immunoconjugates tested were able to suppress growth of the mesothelin positive MiaPaCa-2 tumors in vivo at doses of 0.03 mg/kg, 0.05 mg/kg and 0.2 mg/kg. At doses of 0.05 mg/kg and 0.2 mg/kg of MF-T-SPDB-DM4 complete tumor eradication without regrowth of the tumors occured until the end of the observation period of 132 days. 0.05 mg/kg of the non-targeting control anti-lysozyme-SPDB-DM4 had no effect on the mesothelin positive MiaPaCa tumor growth (Table 1). Compared to untreated and vehicle treated tumors, growth of mesothelin negative HT29 tumors was not significantly reduced by the highest dose of 0.2 mg/kg MF-T-SPDB-DM4. This demonstrates that the strong tumor inhibitory efficacy of MF-T-SPDB-DM4 is dependent on the expression of mesothelin within the tumor.

TABLE 1

Tumor inhibitory efficacy of anti-mesothelin immunconjugates in the mesothelin positive MiaPaCa xenograft tumor model.

| | MF-J-DM4 | MOR-6640-DM4 | MF-T-DM4 | MF-226-DM4 | αLysozyme-DM4 (control) |
|---|---|---|---|---|---|
| DM4/Ab | 2.8 | 3.6 | 3.6 | 3.3 | 4.0-4.1 |
| 0.01 mg/kg | − | − | − | − | n.d. |
| 0.03 mg/kg | n.d. | + | + | + | n.d. |
| 0.05 mg/kg | + | + | ++ a) | + | − |
| 0.2 mg/kg | + | ++ b) | ++ a) | ++ | + b) |

Figure 2:
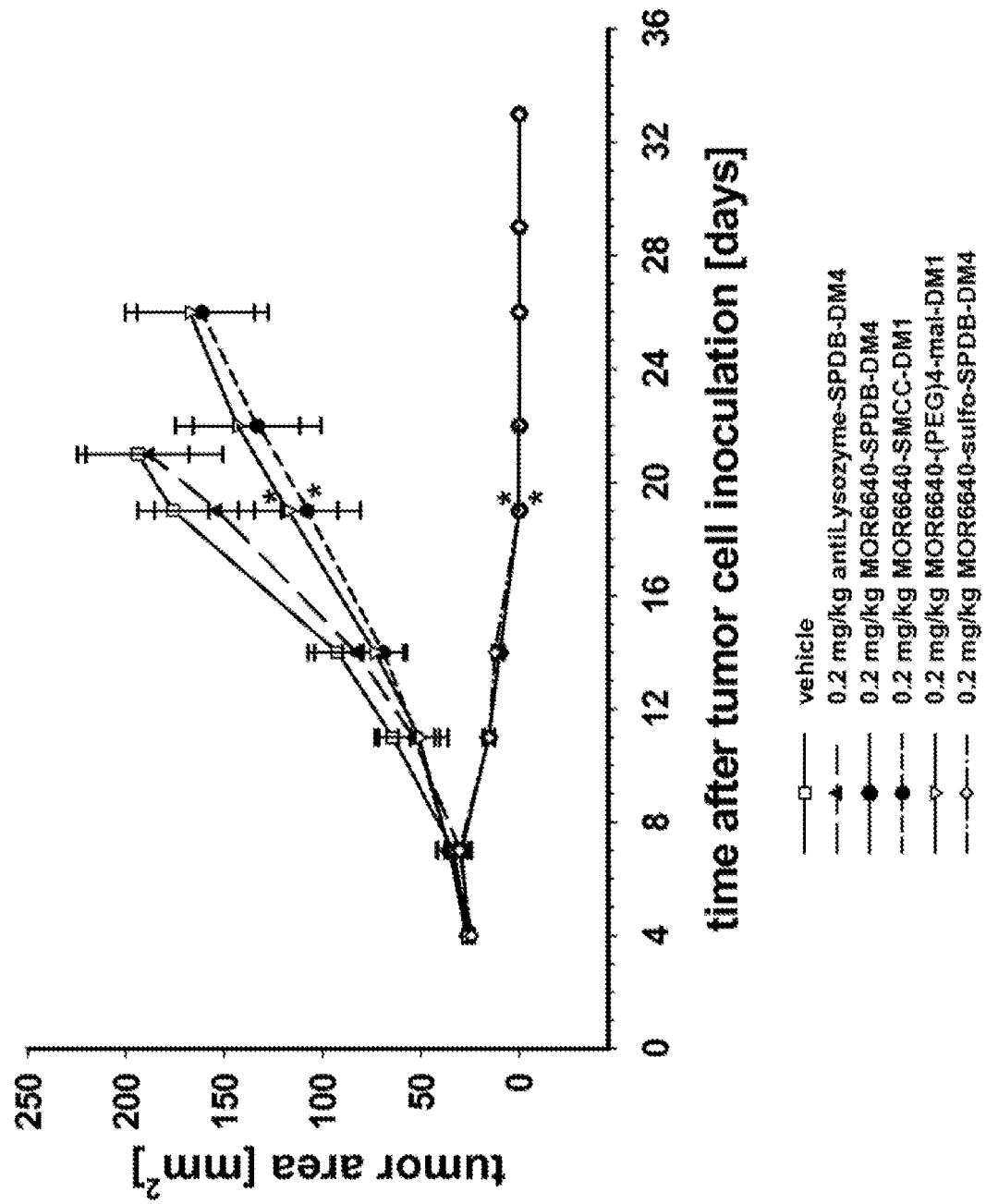
FIG. 2 shows anti-tumor efficacy of anti-mesothelin immunoconjugates with stable and cleavable, as well as polar and nonpolar linkers in a HelaMATU xenograft model with carcinoma cells expressing mesothelin endogenously.
Figure 3A:
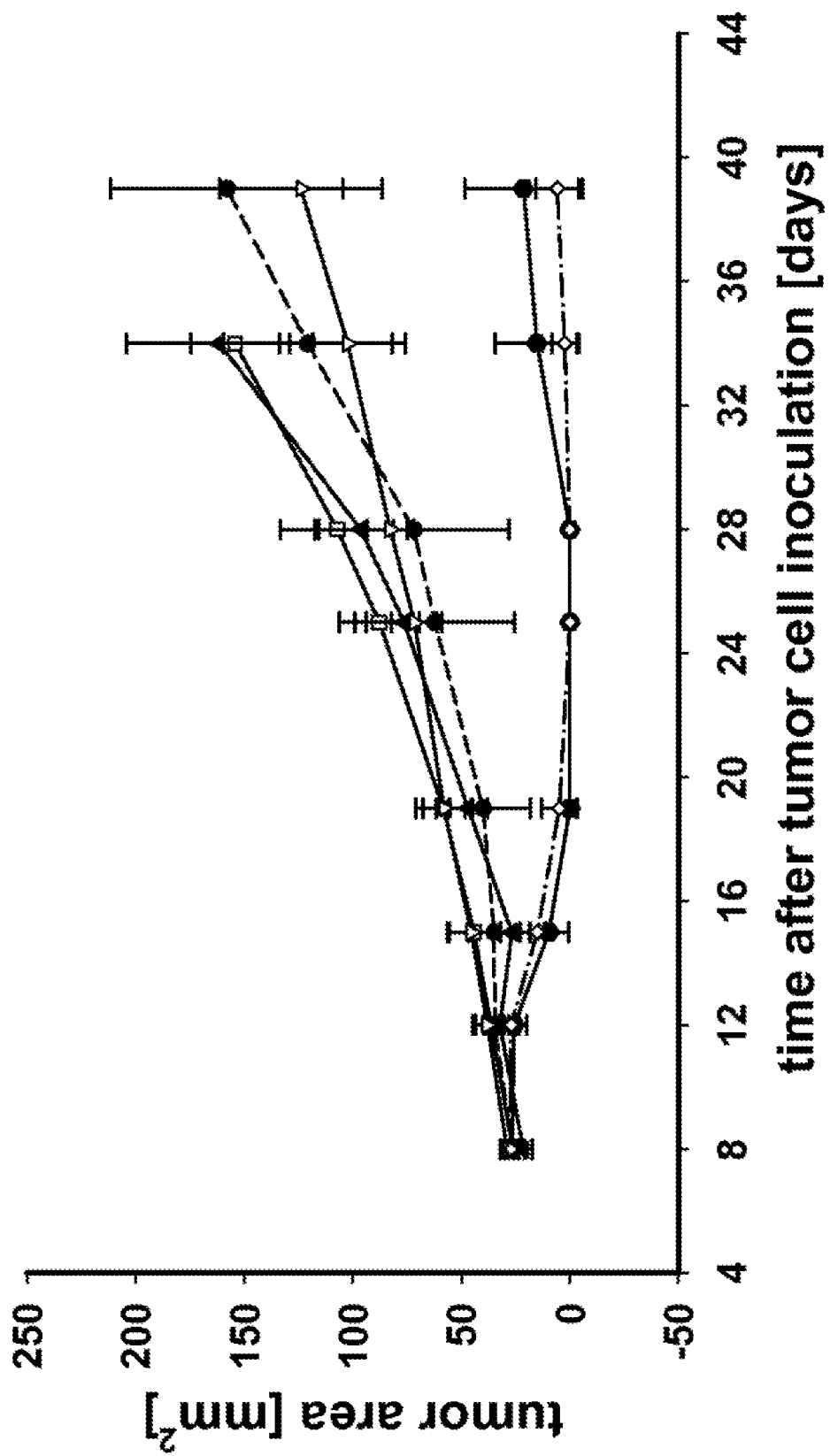
FIGS. 3A-B show anti-tumor efficacy of anti-mesothelin immunoconjugates with stable and cleavable, as well as polar and nonpolar linkers in a mesothelin transfected xenograft model (FIG. 3A) as well as in non-transfected control tumors (FIG. 3B).
Figure 3B:
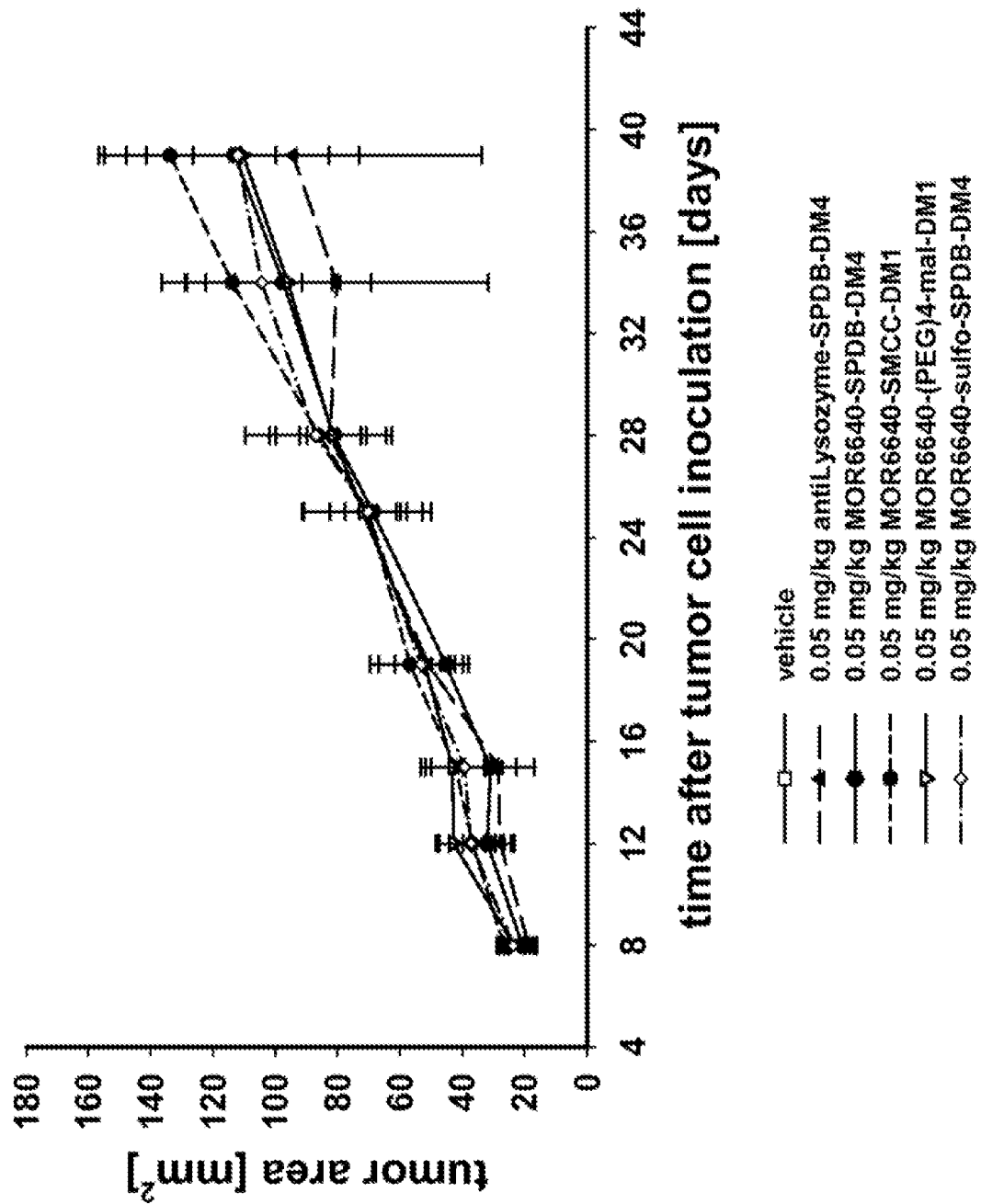

++ tumor eradication
+ reduction/regression
− no sign. Effect, Exp. duration 20-30 d
n.d. not determined
a) Complete eradication over 132 d
b) Tumor regrowth in all animals (n = 6) within 132 d Example 2: Efficacy in Tumors Endogenously Expressing Mesothelin and Comparison of Different Linkers In order to test whether anti-mesothelin immunoconjugates are able to suppress the growth of endogenously mesothelin expressing tumor cells in vivo, a xenograft model with subcutaneously growing human cervix carcinoma cells (HeLaMATU) was used. HeLaMATU cells were maintained as adherent cultures in DMEM/HAMS12 medium supplemented with 10% (v/v) FCS, 2.5% (v/v) horse serum, 1% sodium pyruvate, and 1% (w/v) glutamine. Mesothelin expression was confirmed by FACS analysis in vitro. Female NMRI nude mice were subcutaneously inoculated with $1.5\times10^6$ HeLaMATU cells resuspended in 50% Matrigel™/50% Medium, into the right flank. Additionally it was addressed whether exchange of the cleavable SPDB-linker by a polar (-sulfo-SPDB), by a stable linker (-SMCC), or by a polar and stable linker (-(PEG)4-mal) leads to an altered anti-tumor efficacy of the MOR6640-based immunoconjugate in vivo. HeLaMATU tumor-bearing mice were treated intravenously with 0.2 mg/kg of either MOR6640-SPDB-DM4, MOR6640-SMCC-DM1, MOR6640-Sulfo-SPDB-DM4, or MOR6640-(PEG)4-mal-DM1 (related to the amount of toxophore) at day 5, 8, and 12 after tumor cell inoculation. Control mice were either treated with 0.2 mg/kg of the non-targeting immunoconjugate (anti-lysozyme-SPDB-DM4) or with equal volumes of vehicle alone Groups consisted of 6 animals each. Daily examination of the health status of the mice was conducted. Length and width of the subcutaneous tumors were measured using an electronic caliper twice per week. Tumor area was calculated by the formula: tumor area $[mm^2]$=length [mm]×width [mm]. Data obtained are presented in FIG. 2. Treatment of the tumor-bearing mice revealed a) that anti-mesothelin immunoconjugates were efficacious in suppressing growth of tumors expressing mesothelin endogenously in vivo and b) that conjugates with cleavable linkers (MOR6640-SPDB-DM4 and MOR6640) displayed a higher anti-tumor efficacy than the conjugates with stable linkers (MOR6640-SMCC-DM1 and MOR6640-(PEG)4-mal-DM1). In particular, MOR6640-SPDB-DM4 and MOR6640-sulfo-SPDB-DM4 led to an eradication of the tumors of all treated animals eleven days after the last treatment, whereas treatment with MOR6640-SMCC-DM1 and MOR6640-(PEG)4-mal-DM1 resulted only in a delay of tumor growth. However, eleven days after the last treatment the area of tumors treated with MOR6640-SMCC-DM1 and MOR6640-(PEG)4-mal-DM1, respectively, were significantly smaller as compared to vehicle or anti-lysozyme-SPDB-DM4 treated tumors. The non-targeting control conjugate had no effect on tumor growth. In order to compare the anti-tumor efficacy of the different linkers in a second xenograft model, we employed the model with subcutaneously growing vector- or mesothelin-transfected (#37) MiaPaCa-2 cells (human pancreas carcinoma cells). MiaPaCa-2-vector and MiaPaCa-2#37 cells were maintained as adherent cultures in DMEM/HAMS12 medium supplemented with 10% (v/v) FCS, 1% (w/v) glutamine, and 0.1 mM non-essential amino acids. Mesothelin expression was confirmed by FACS analysis and by immunohistochemical analysis of subcutaneous tumors ex vivo. Female NMRI nude mice were subcutaneously inoculated with $3 \times 10^6$ MiaPaCa-2-vector and MiaPaCa-2#37 cells, resuspended in 50% Matrigel™/50% Medium, respectively, into the right flank. Tumor-bearing mice were treated with 0.05 mg/kg of either MOR6640-SPDB-DM4, MOR6640-SMCC-DM1, MOR6640-Sulfo-SPDB-DM4, or MOR6640-(PEG)4-mal-DM1 (related to the amount of toxophore) at day 5, 8, and 12 after tumor cell inoculation. Control mice were either treated with 0.05 mg/kg of the non-targeting immunoconjugate (anti-lysozyme-SPDB-DM4) or with equal volumes of vehicle alone. Groups consisted of 6 animals each. Daily examination of the health status of the mice was conducted. Length and width of the subcutaneous tumors were measured using an electronic caliper twice per week. Tumor area was calculated by the formula: tumor area [mm$^2$]=length [mm]×width [mm]. Tumor growth data are presented in FIG. 3. In mice bearing mesothelin expressing tumors, treatment with MOR6640-SPDB-DM4 and MOR6640-sulfo-SPDB-DM4 led to an eradication of the tumors of all treated animals 12 days after the last treatment. However, re-growth of these tumors was obtained ten days later (FIG. 3A). Treatment with MOR6640-SMCC-DM1, MOR6640-(PEG)4-mal-DM1, and anti-lysozyme-SPDB-DM4 did not affect tumor growth significantly. In contrast to mesothelin expressing tumors, none of the treatments led to an altered growth of the vector-transfected MiaPaCa-2 cells in vivo (FIG. 3B).

Example 3: In Vitro Cytotoxicity of Anti-Mesothelin Immunoconjugates

Figure 4:
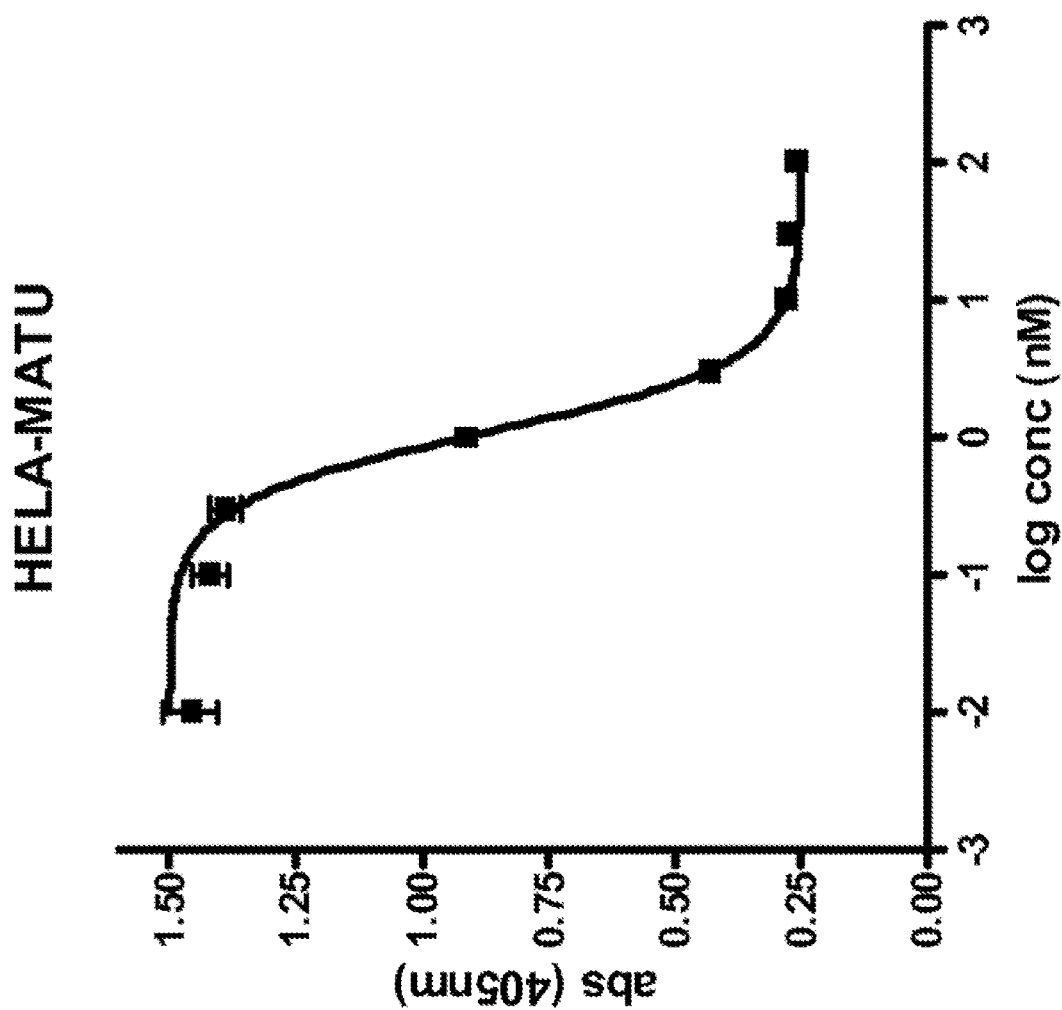
FIG. 4 shows an example of a dose response curve of MF-T-SPDP-DM4 toxicity on mesothelin positive Hela-Matu cells.

To assess cytotoxicity of anti-mesothelin immunoconjugates, different meseothelin expressing cell lines were grown to 80-90% confluence, trypsinized and counted. Cells were then seeded into 384-well flat bottom plates at 800 with 25 ul of volume per well in their growth media for all cell lines. Media only wells were set up for blank subtraction. At 24 hr post seeding, MF-J-SPDB-DM4, MF-226-SPDB-DM4 MOR6640-SPDP-DM4, MF226-SPDP-DM4 and anti-Lysozyme-SPDP-DM4 were dosed at the range of 0.01 to 3 00 nM. Triplicates were set up for each dilution. Endpoint measurements were performed at 96 hrs. Cell viability was assessed by WST-1 assay measurement (Roche Cat #1644807). IC$_{50}$ values are shown in Table 2. A dose-reponse curve demonstrating in vitro cytotoxicity of MF-T-SPDP-DM4 on HelaMatu cells is shown in FIG. 4.

TABLE 2 nM IC$_{50}$ values of anti-mesothelin immunoconjugates on mesothelin expressing cell lines

| IC50 (nM) | MF-J-SPDP-DM4 | MOR06640-SPDP-DM4 | MF-T-SPDP-DM4 | MF-226-SPDP-DM4 | αLysozyme-SPDP-DM4 (control) |
|---|---|---|---|---|---|
| MiaPaCa-2 (Mesothelin+) | 1.4 | 0.36 | 1.3 | 21 | >100 |
| MiaPaCa-2 (Mesothelin−) | >100 | >100 | >100 | >100 | >100 |
| HT29 C2 (Mesothelin+) | 0.3 | 0.21 | 1.5 | 8 | 18 |
| HT29 V (Mesothelin−) | >50 | >50 | >50 | >50 | >50 |
| CHO A9* (Mesothelin+) | 0.35 | 1.2 | 1.0 | 1.3 | >50 |
| CHO K1* (Mesothelin−) | >50 | >50 | >50 | >50 | >50 |
| DU145 | 5.2 | 5.1 | 9 | 10 | — |
| HCT116 | 9.0 | 20.7 | 17.2 | 26.5 | 33.1 |
| SW480 | >50 | >50 | >50 | >50 | >50 |
| MDAMB231 | >50 | >50 | >50 | >50 | >50 |
| MCF10a | >50 | >50 | >50 | >50 | >50 |
| HelaMatu | 0.2 | 0.6 | 0.45 | 0.9 | 0.4 |
| OVCAR-3 | 0.9 | 1.07 | 2.8 | 14.8 | >100 |
| KD of Fab (nM) | 9.2 | 0.19 | 16.3 | 58.3 | |

TABLE 3

Sequences of antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| MF-J | 1 | 4 | 7 | 10 | 13 | 16 | 20 | 24 | 28 | 32 |
| MOR 06640 | 1 | 4 | 7 | 10 | 13 | 17 | 21 | 25 | 29 | 33 |
| MF-226 | 2 | 5 | 8 | 11 | 14 | 18 | 22 | 26 | 30 | 34 |
| MF-T | 3 | 6 | 9 | 12 | 15 | 19 | 23 | 27 | 31 | 35 |

What is claimed is:

1. An immunoconjugate comprising an antibody and the maytansinoid DM4 wherein said antibody comprises a variable heavy chain (VH) of SEQ ID NO: 23 and a variable light chain (VL) of SEQ ID NO: 27 and wherein said antibody and said maytansinoid DM4 are linked via a SPDB linker.

2. A pharmaceutical composition comprising an immunoconjugate according to claim 1 and a pharmaceutically acceptable carrier or excipient therefore.

* * * * *